United States Patent
Kraus et al.

(10) Patent No.: US 9,599,606 B2
(45) Date of Patent: Mar. 21, 2017

(54) ADP-RIBOSE DETECTION REAGENTS

(71) Applicant: The Board of Regents of the University of Texas System, Austin, TX (US)

(72) Inventors: W. Lee Kraus, Coppell, TX (US); Bryan A. Gibson, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/734,780

(22) Filed: Jun. 9, 2015

(65) Prior Publication Data

US 2015/0355172 A1     Dec. 10, 2015

Related U.S. Application Data

(60) Provisional application No. 62/009,955, filed on Jun. 10, 2014.

(51) Int. Cl.
| | |
|---|---|
| *G01N 33/53* | (2006.01) |
| *C12N 9/00* | (2006.01) |
| *C07K 14/00* | (2006.01) |
| *C12Q 1/48* | (2006.01) |
| *G01N 33/574* | (2006.01) |

(52) U.S. Cl.
CPC ......... *G01N 33/5308* (2013.01); *C07K 14/00* (2013.01); *C12N 9/93* (2013.01); *C12Q 1/48* (2013.01); *G01N 33/57484* (2013.01); *C12Y 603/02019* (2013.01); *G01N 2333/9015* (2013.01); *G01N 2333/91142* (2013.01); *G01N 2400/00* (2013.01)

(58) Field of Classification Search
None
See application file for complete search history.

(56) References Cited

U.S. PATENT DOCUMENTS

| | | | |
|---|---|---|---|
| 6,468,794 B1 | 10/2002 | Uchida et al. | |
| 7,105,150 B2 | 9/2006 | Buck et al. | |
| 7,153,686 B2 | 12/2006 | Uchida et al. | |
| 8,937,157 B2 * | 1/2015 | Ledbetter | C07K 16/46 424/184.1 |
| 2002/0142406 A1 * | 10/2002 | Skraly | C08G 8/04 435/135 |
| 2007/0041999 A1 * | 2/2007 | Rasochova | C07K 14/005 424/204.1 |

OTHER PUBLICATIONS

Ahel et al., "Poly(ADP-ribose)-binding zinc finger motifs in DNA repair/checkpoint proteins," *Nature*, 451(7174):81-85, 2008.
Ahel et al., "Poly(ADP-ribose)-dependent regulation of DNA repair by the chromatin remodeling enzyme ALC1," *Science*, 325:1240-1243, 2009.
Egloff et al., "Structural and functional basis for ADP-ribose and poly(ADP-ribose) binding by viral macro domains," *J. Virol.*, 80(17):8493-8502, 2006.
Gibson and Kraus, "New insights into the molecular and cellular functions of poly(ADP-ribose) and PARPs," *Nature Rev Mol Cell Biol*, 13(7):411-424, 2012.
Gottschalk et al., "Poly(ADP-ribosyl)ation directs recruitment and activation of an ATP-dependent chromatin remodeler," *Proc Natl Acad Sci USA*, 106:13770-13774, 2009.
He et al., "Structural insight into the interaction of ADP-ribose with the PARP WWE domains," *FEBS Lett*, 586:3858-3864, 2012.
Karras et al., "The macro domain is an ADP-ribose binding module," *EMBO J*, 24(11):1911-1920, 2005.
Oliver-De la Cruz and Ayuso-Sacido, "Neural stem cells from mammalian brain: isolation protocols and maintenance conditions," *Neural Stem Cells and Therapy*, Dr. Tao Sun (Ed.), Chapter 1, 2012.
Pleschke et al., "Poly(ADP-ribose) binds to specific domains in DNA damage checkpoint proteins," *J. Biol Chem.*, 275(52):40974-40980, 2000.
Timinszky et al., "A macrodomain-containing histone rearranges chromatin upon sensing PARP1 activation," *Nat Struct Mol Biol.*, 16:923-929, 2009.
Wang et al., "Recognition of the iso-ADP-ribose moiety in poly(ADP-ribose) by WWE domains suggest a general mechanism for poly (ADP-ribosyl)ation-dependent ubiquitination," *Genes Dev.*, 26(3):235-240, 2012.
Carter et al., "Fusion partners can increase the expression of recombinant interleukins via transient transfection in 2936E cells," *Protein Sci*, 19(2):357-362, 2010.
He et al., "Structural insight into the interaction of ADP-ribose with PARP WWE domains," *FEBS Lett*, 586(21):3858-3864, 2012.
InvivoGen, "pFUSE-Fc Vectors," retrieved from https://web.archive.org/web/20140222233939/http://www.invivogen.com/pfuse-fc, dated Feb. 22, 2014, downloaded Sep. 1, 2015.
InvivoGen, "pFUSE-h1gGl-Fcl—Plasmid designed for the construction of Fc-Fusion proteins," retrieved from https://web.archive.org/web/20140223112418/http://www.invivogen.com/fc-fusions, dated Feb. 23, 2014, downloaded Sep. 1, 2015.
Li et al., "The FHA and BRCT domains recognize ADP-ribosylation during DNA damage response," *Genes Dev*, 27(16):1752-1768, 2013.
PCT International Search Report and Written Opinion issued in International Application No. PCT/US2015/034852, mailed Jan. 11, 2016.

* cited by examiner

*Primary Examiner* — Jacob Cheu
(74) *Attorney, Agent, or Firm* — Parker Highlander PLLC

(57) ABSTRACT

The present disclosure described fusion proteins between ADP-ribose binding domains and antibody Fc domains. This new class of reagents has considerable value as detection agents in assays designed at examining the biology of ADP-ribose.

42 Claims, 8 Drawing Sheets

ADP-Ribose Binding Domain-Fc Fusion Proteins

| His₁₀ | Strep(II) | ADP-ribose Binding Domain | Gly-Ser Linker | Rabbit Fc Domain |
|---|---|---|---|---|

Natural ADP-ribose binding domains used:

1) WWE(RNF146) = RNF146 WWE domain from *Homo sapiens* (Human).

2) Macro(AF1521) = AF1521 macrodomain from *Archaeoglobus fulgidus* (Archeabacterium).

3) Macro(mH2A1.1) = MacroH2A1.1 macrodomain from *Homo sapiens* (Human).

4) Macro3X(PARP14) = Macrodomains 1 through 3 of PARP14 from *Homo sapiens* (Human).

FIG. 1.1-1.5

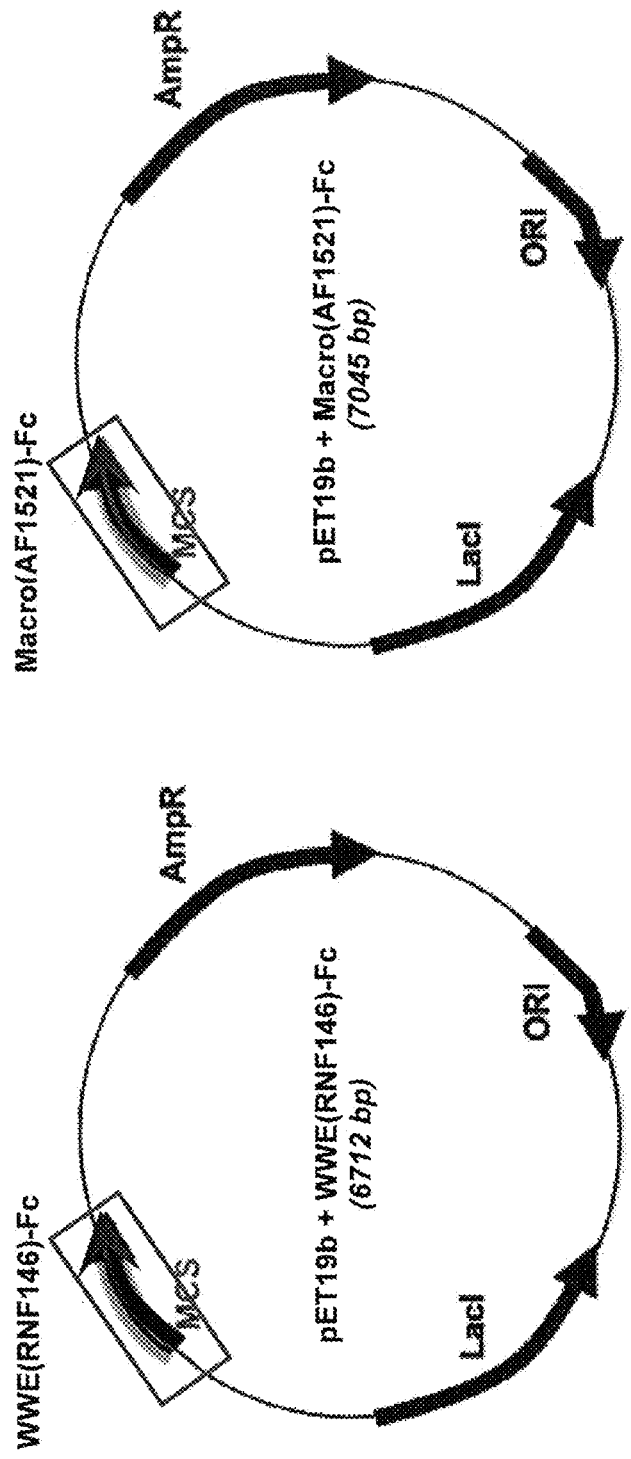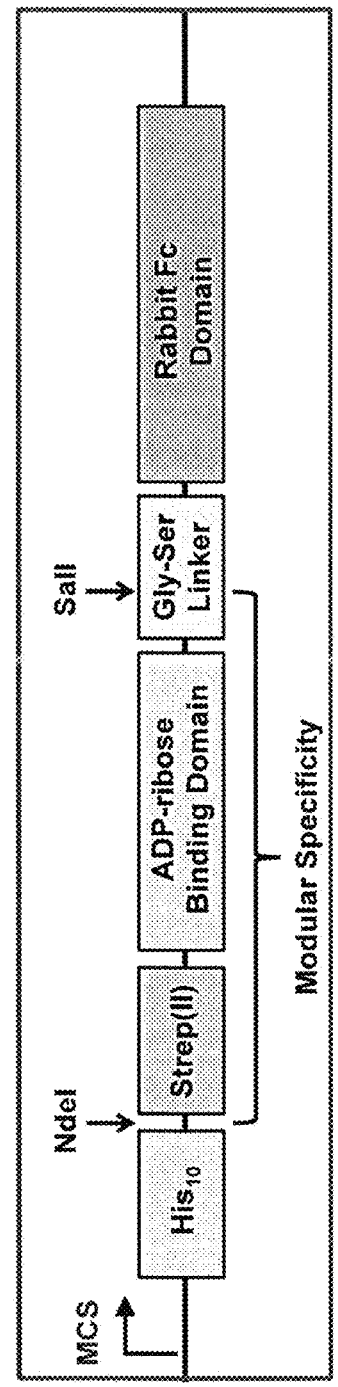
FIG. 2
**The plasmid vectors for expressing Macro(mH2A1.1)-Fc and Macro3X(PARP14)-Fc are constructed in a similar manner.

SEQUENCE LISTING

```
<160> NUMBER OF SEQ ID NOS: 11

<210> SEQ ID NO 1
<211> LENGTH: 349
<212> TYPE: PRT
<213> ORGANISM: Artificial sequence
<220> FEATURE:
<223> OTHER INFORMATION: Synthetic fusion peptide

<400> SEQUENCE: 1

Met Gly His His His His His His His His Ser Ser Gly His
1               5                   10                  15

Ile Asp Asp Asp Lys His Met Trp Ser His Pro Gln Phe Glu Lys
                20                  25                  30

Gly Ser Ser Gly Asn Gly Glu Tyr Ala Trp Tyr Tyr Glu Gly Arg Asn
            35                  40                  45

Gly Trp Trp Gln Tyr Asp Glu Arg Thr Ser Arg Glu Leu Glu Asp Ala
        50                  55                  60

Phe Ser Lys Gly Lys Lys Asn Thr Glu Met Leu Ile Ala Gly Phe Leu
65                  70                  75                  80

Tyr Val Ala Asp Leu Glu Asn Met Val Gln Tyr Arg Arg Asn Glu His
                85                  90                  95

Gly Arg Arg Arg Lys Ile Lys Arg Asp Ile Ile Asp Ile Pro Lys Lys
            100                 105                 110

Gly Val Ala Gly Leu Arg Leu Asp Gly Ser Thr Gly Ser Ser Ser Lys
        115                 120                 125

Pro Thr Cys Pro Pro Pro Glu Leu Leu Gly Gly Pro Ser Val Phe Ile
130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Asp Pro Glu Val Gln
                165                 170                 175

Phe Thr Trp Tyr Ile Asn Asn Glu Gln Val Arg Thr Ala Arg Pro Pro
            180                 185                 190

Leu Arg Glu Gln Gln Phe Asn Ser Thr Ile Arg Val Val Ser Thr Leu
        195                 200                 205

Pro Ile Ala His Gln Asp Trp Leu Arg Gly Lys Glu Phe Lys Cys Lys
    210                 215                 220

Val His Asn Lys Ala Leu Pro Ala Pro Ile Glu Lys Thr Ile Ser Lys
225                 230                 235                 240

Ala Arg Gly Gln Pro Leu Glu Pro Lys Val Tyr Thr Met Gly Pro Pro
                245                 250                 255

Arg Glu Glu Leu Ser Ser Arg Ser Val Ser Leu Thr Cys Met Ile Asn
            260                 265                 270

Gly Phe Tyr Pro Ser Asp Ile Ser Val Glu Trp Glu Lys Asn Gly Lys
        275                 280                 285
```

Ala Glu Asp Asn Tyr Lys Thr Thr Pro Ala Val Leu Asp Ser Asp Gly
290                 295                 300

Ser Tyr Phe Leu Tyr Ser Lys Leu Ser Val Pro Thr Ser Glu Trp Gln
305                 310                 315                 320

Arg Gly Asp Val Phe Thr Cys Ser Val Met His Glu Ala Leu His Asn
                325                 330                 335

His Tyr Thr Gln Lys Ser Ile Ser Arg Ser Pro Gly Lys
                340                 345

<210> SEQ ID NO 2
<211> LENGTH: 460
<212> TYPE: PRT
<213> ORGANISM: Artificial sequence
<220> FEATURE:
<223> OTHER INFORMATION: Synthetic fusion peptide

<400> SEQUENCE: 2

Met Gly His His His His His His His His Ser Ser Gly His
1               5                   10                  15

Ile Asp Asp Asp Lys His Met Trp Ser His Pro Gln Phe Glu Lys
                20                  25                  30

Met Glu Arg Arg Thr Leu Ile Met Glu Val Leu Phe Glu Ala Lys Val
                35                  40                  45

Gly Asp Ile Thr Leu Lys Leu Ala Gln Gly Asp Ile Thr Gln Tyr Pro
    50                  55                  60

Ala Lys Ala Ile Val Asn Ala Ala Asn Lys Arg Leu Glu His Gly Gly
65                  70                  75                  80

Gly Val Ala Tyr Ala Ile Ala Lys Ala Cys Ala Gly Asp Ala Gly Leu
                85                  90                  95

Tyr Thr Glu Ile Ser Lys Lys Ala Met Arg Glu Gln Phe Gly Arg Asp
                100                 105                 110

Tyr Ile Asp His Gly Glu Val Val Thr Pro Ala Met Asn Leu Glu
                115                 120                 125

Glu Arg Gly Ile Lys Tyr Val Phe His Thr Val Gly Pro Ile Cys Ser
    130                 135                 140

Gly Met Trp Ser Glu Glu Leu Lys Glu Lys Leu Tyr Lys Ala Phe Leu
145                 150                 155                 160

Gly Pro Leu Glu Lys Ala Glu Glu Met Gly Val Glu Ser Ile Ala Phe
                165                 170                 175

Pro Ala Val Ser Ala Gly Ile Tyr Gly Cys Asp Leu Glu Lys Val Val
                180                 185                 190

Glu Thr Phe Leu Glu Ala Val Lys Asn Phe Lys Gly Ser Ala Val Lys
    195                 200                 205

Glu Val Ala Leu Val Ile Tyr Asp Arg Lys Ser Ala Glu Val Ala Leu
    210                 215                 220

Lys Val Phe Glu Arg Ser Leu Gly Ser Thr Gly Ser Ser Ser Lys Pro
225                 230                 235                 240

Thr Cys Pro Pro Pro Glu Leu Leu Gly Gly Pro Ser Val Phe Ile Phe
                245                 250                 255

Pro Pro Lys Pro Lys Asp Thr Leu Met Ile Ser Arg Thr Pro Glu Val
                260                 265                 270

Thr Cys Val Val Val Asp Val Ser Gln Asp Asp Pro Glu Val Gln Phe
    275                 280                 285

Thr Trp Tyr Ile Asn Asn Glu Gln Val Arg Thr Ala Arg Pro Pro Leu
    290                 295                 300

```
Arg Glu Gln Gln Phe Asn Ser Thr Ile Arg Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Ala Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460

<210> SEQ ID NO 3
<211> LENGTH: 462
<212> TYPE: PRT
<213> ORGANISM: Artificial sequence
<220> FEATURE:
<223> OTHER INFORMATION: Synthetic fusion peptide

<400> SEQUENCE: 3

Met Gly His His His His His His His His Ser Ser Gly His
1               5                   10                  15

Ile Asp Asp Asp Lys His Met Gly Glu Val Ser Lys Ala Ala Ser
                20                  25                  30

Ala Asp Ser Thr Thr Glu Gly Thr Pro Ala Asp Gly Phe Thr Val Leu
            35                  40                  45

Ser Thr Lys Ser Leu Phe Leu Gly Gln Lys Leu Gln Val Val Gln Ala
    50                  55                  60

Asp Ile Ala Ser Ile Asp Ser Asp Ala Val His Pro Thr Asn Thr
65                  70                  75                  80

Asp Phe Tyr Ile Gly Gly Glu Val Gly Asn Thr Leu Glu Lys Lys Gly
                85                  90                  95

Gly Lys Glu Phe Val Glu Ala Val Leu Glu Leu Arg Lys Lys Asn Gly
            100                 105                 110

Pro Leu Glu Val Ala Gly Ala Ala Val Ser Ala Gly His Gly Leu Pro
        115                 120                 125

Ala Lys Phe Val Ile His Cys Asn Ser Pro Val Trp Gly Ala Asp Lys
    130                 135                 140

Cys Glu Glu Leu Leu Glu Lys Thr Val Lys Asn Cys Leu Ala Leu Ala
145                 150                 155                 160

Asp Asp Lys Lys Leu Lys Ser Ile Ala Phe Pro Ser Ile Gly Ser Gly
                165                 170                 175

Arg Asn Gly Phe Pro Lys Gln Thr Ala Ala Gln Leu Ile Leu Lys Ala
            180                 185                 190

Ile Ser Ser Tyr Phe Val Ser Thr Met Ser Ser Ser Ile Lys Thr Val
        195                 200                 205
```

```
Tyr Phe Val Leu Phe Asp Ser Glu Ser Ile Gly Ile Tyr Val Gln Glu
    210                 215                 220

Met Ala Lys Leu Asp Ala Asn Leu Asp Gly Ser Thr Gly Ser Ser Ser
225                 230                 235                 240

Lys Pro Thr Cys Pro Pro Glu Leu Leu Gly Gly Pro Ser Val Phe
                245                 250                 255

Ile Phe Pro Pro Lys Pro Lys Asp Thr Leu Met Ile Ser Arg Thr Pro
                260                 265                 270

Glu Val Thr Cys Val Val Val Asp Val Ser Gln Asp Asp Pro Glu Val
                275                 280                 285

Gln Phe Thr Trp Tyr Ile Asn Asn Glu Gln Val Arg Thr Ala Arg Pro
    290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
                340                 345                 350

Lys Ala Arg Gly Gln Pro Leu Glu Pro Lys Val Tyr Thr Met Gly Pro
    355                 360                 365

Pro Arg Glu Glu Leu Ser Ser Arg Ser Val Ser Leu Thr Cys Met Ile
370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Ala Val Leu Asp Ser Asp
                405                 410                 415

Gly Ser Tyr Phe Leu Tyr Ser Lys Leu Ser Val Pro Thr Ser Glu Trp
                420                 425                 430

Gln Arg Gly Asp Val Phe Thr Cys Ser Val Met His Glu Ala Leu His
    435                 440                 445

Asn His Tyr Thr Gln Lys Ser Ile Ser Arg Ser Pro Gly Lys
    450                 455                 460

<210> SEQ ID NO 4
<211> LENGTH: 899
<212> TYPE: PRT
<213> ORGANISM: Artificial sequence
<220> FEATURE:
<223> OTHER INFORMATION: Synthetic fusion peptide

<400> SEQUENCE: 4

Met Gly His His His His His His His His Ser Ser Gly His
1               5                   10                  15

Ile Asp Asp Asp Lys His Met Thr Asp Lys Pro Gly Ala Lys Gln
            20                  25                  30

Phe Phe Gln Asp Lys Ala Arg Phe Tyr Gln Ser Glu Ile Lys Arg Leu
        35                  40                  45

Phe Gly Cys Tyr Ile Glu Leu Gln Glu Asn Glu Val Met Lys Glu Gly
    50                  55                  60

Gly Ser Pro Ala Gly Gln Lys Cys Phe Ser Arg Thr Val Leu Ala Pro
65                  70                  75                  80

Gly Val Val Leu Ile Val Gln Gln Gly Asp Leu Ala Arg Leu Pro Val
                85                  90                  95

Asp Val Val Asn Ala Ser Asn Glu Asp Leu Lys His Tyr Gly Gly
            100                 105                 110
```

```
Leu Ala Ala Ala Leu Ser Lys Ala Ala Gly Pro Glu Leu Gln Ala Asp
            115                 120                 125

Cys Asp Gln Ile Val Lys Arg Glu Gly Arg Leu Leu Pro Gly Asn Ala
130                 135                 140

Thr Ile Ser Lys Ala Gly Lys Leu Pro Tyr His His Val Ile His Ala
145                 150                 155                 160

Val Gly Pro Arg Trp Ser Gly Tyr Glu Ala Pro Arg Cys Val Tyr Leu
                165                 170                 175

Leu Arg Arg Ala Val Gln Leu Ser Leu Cys Leu Ala Glu Lys Tyr Lys
            180                 185                 190

Tyr Arg Ser Ile Ala Ile Pro Ala Ile Ser Ser Gly Val Phe Gly Phe
        195                 200                 205

Pro Leu Gly Arg Cys Val Glu Thr Ile Val Ser Ala Ile Lys Glu Asn
    210                 215                 220

Phe Gln Phe Lys Lys Asp Gly His Cys Leu Lys Glu Ile Tyr Leu Val
225                 230                 235                 240

Asp Val Ser Glu Lys Thr Val Glu Ala Phe Ala Glu Ala Val Lys Thr
                245                 250                 255

Val Phe Lys Ala Thr Leu Pro Asp Thr Ala Ala Pro Pro Gly Leu Pro
            260                 265                 270

Pro Ala Ala Ala Gly Pro Gly Lys Thr Ser Trp Glu Lys Gly Ser Leu
        275                 280                 285

Val Ser Pro Gly Gly Leu Gln Met Leu Leu Val Lys Glu Gly Val Gln
    290                 295                 300

Asn Ala Lys Thr Asp Val Val Asn Ser Val Pro Leu Asp Leu Val
305                 310                 315                 320

Leu Ser Arg Gly Pro Leu Ser Lys Ser Leu Leu Glu Lys Ala Gly Pro
                325                 330                 335

Glu Leu Gln Glu Glu Leu Asp Thr Val Gly Gln Gly Val Ala Val Ser
            340                 345                 350

Met Gly Thr Val Leu Lys Thr Ser Ser Trp Asn Leu Asp Cys Arg Tyr
        355                 360                 365

Val Leu His Val Ala Pro Glu Trp Arg Asn Gly Ser Thr Ser Ser
    370                 375                 380

Leu Lys Ile Met Glu Asp Ile Ile Arg Glu Cys Met Glu Ile Thr Glu
385                 390                 395                 400

Ser Leu Ser Leu Lys Ser Ile Ala Phe Pro Ala Ile Gly Thr Gly Asn
                405                 410                 415

Leu Gly Phe Pro Lys Asn Ile Phe Ala Glu Leu Ile Ile Ser Glu Val
            420                 425                 430

Phe Lys Phe Ser Ser Lys Asn Gln Leu Lys Thr Leu Gln Glu Val His
        435                 440                 445

Phe Leu Leu His Pro Ser Asp His Glu Asn Ile Gln Ala Phe Ser Asp
    450                 455                 460

Glu Phe Ala Arg Arg Ala Asn Gly Asn Leu Val Ser Asp Lys Ile Pro
465                 470                 475                 480

Lys Ala Lys Asp Thr Gln Gly Phe Tyr Gly Thr Val Ser Ser Pro Asp
                485                 490                 495

Ser Gly Val Tyr Glu Met Lys Ile Gly Ser Ile Ile Phe Gln Val Ala
            500                 505                 510

Ser Gly Asp Ile Thr Lys Glu Glu Ala Asp Val Ile Val Asn Ser Thr
        515                 520                 525

Ser Asn Ser Phe Asn Leu Lys Ala Gly Val Ser Lys Ala Ile Leu Glu
```

```
            530                 535                 540
Cys Ala Gly Gln Asn Val Glu Arg Glu Cys Ser Gln Ala Gln Gln
545                 550                 555                 560

Arg Lys Asn Asp Tyr Ile Ile Thr Gly Gly Phe Leu Arg Cys Lys
                565                 570                 575

Asn Ile Ile His Val Ile Gly Gly Asn Asp Val Lys Ser Ser Val Ser
                580                 585                 590

Ser Val Leu Gln Glu Cys Glu Lys Lys Asn Tyr Ser Ser Ile Cys Leu
                595                 600                 605

Pro Ala Ile Gly Thr Gly Asn Ala Lys Gln His Pro Asp Lys Val Ala
610                 615                 620

Glu Ala Ile Ile Asp Ala Ile Glu Asp Phe Val Gln Lys Gly Ser Ala
625                 630                 635                 640

Gln Ser Val Lys Lys Val Lys Val Val Ile Phe Leu Pro Gln Val Leu
                645                 650                 655

Asp Val Phe Tyr Ala Asn Met Lys Lys Arg Glu Gly Leu Asp Gly Ser
                660                 665                 670

Thr Gly Ser Ser Ser Lys Pro Thr Cys Pro Pro Glu Leu Leu Gly
                675                 680                 685

Gly Pro Ser Val Phe Ile Phe Pro Pro Lys Pro Lys Asp Thr Leu Met
690                 695                 700

Ile Ser Arg Thr Pro Glu Val Thr Cys Val Val Val Asp Val Ser Gln
705                 710                 715                 720

Asp Asp Pro Glu Val Gln Phe Thr Trp Tyr Ile Asn Asn Glu Gln Val
                725                 730                 735

Arg Thr Ala Arg Pro Pro Leu Arg Glu Gln Gln Phe Asn Ser Thr Ile
                740                 745                 750

Arg Val Val Ser Thr Leu Pro Ile Ala His Gln Asp Trp Leu Arg Gly
                755                 760                 765

Lys Glu Phe Lys Cys Lys Val His Asn Lys Ala Leu Pro Ala Pro Ile
                770                 775                 780

Glu Lys Thr Ile Ser Lys Ala Arg Gly Gln Pro Leu Glu Pro Lys Val
785                 790                 795                 800

Tyr Thr Met Gly Pro Pro Arg Glu Glu Leu Ser Arg Ser Val Ser
                805                 810                 815

Leu Thr Cys Met Ile Asn Gly Phe Tyr Pro Ser Asp Ile Ser Val Glu
                820                 825                 830

Trp Glu Lys Asn Gly Lys Ala Glu Asp Asn Tyr Lys Thr Thr Pro Ala
                835                 840                 845

Val Leu Asp Ser Asp Gly Ser Tyr Phe Leu Tyr Ser Lys Leu Ser Val
850                 855                 860

Pro Thr Ser Glu Trp Gln Arg Gly Asp Val Phe Thr Cys Ser Val Met
865                 870                 875                 880

His Glu Ala Leu His Asn His Tyr Thr Gln Lys Ser Ile Ser Arg Ser
                885                 890                 895

Pro Gly Lys

<210> SEQ ID NO 5
<211> LENGTH: 10
<212> TYPE: PRT
<213> ORGANISM: Artificial sequence
<220> FEATURE:
<223> OTHER INFORMATION: Synthetic peptide linker

<400> SEQUENCE: 5
```

Gly Gly Gly Gly Ser Gly Gly Gly Gly Ser
1               5                   10

<210> SEQ ID NO 6
<211> LENGTH: 15
<212> TYPE: PRT
<213> ORGANISM: Artificial sequence
<220> FEATURE:
<223> OTHER INFORMATION: Synthetic peptide linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 20
<212> TYPE: PRT
<213> ORGANISM: Artificial sequence
<220> FEATURE:
<223> OTHER INFORMATION: Synthetic peptide linker

<400> SEQUENCE: 7

Gly Gly Gly Gly Ser Gly Gly Gly Gly Ser Gly Gly Gly Gly Ser Gly
1               5                   10                  15

Gly Gly Gly Ser
            20

<210> SEQ ID NO 8
<211> LENGTH: 25
<212> TYPE: PRT
<213> ORGANISM: Artificial sequence
<220> FEATURE:
<223> OTHER INFORMATION: Synthetic peptide linker

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 9
<211> LENGTH: 10
<212> TYPE: PRT
<213> ORGANISM: Artificial sequence
<220> FEATURE:
<223> OTHER INFORMATION: Synthetic peptide linker

<400> SEQUENCE: 9

Glu Ala Ala Ala Lys Glu Ala Ala Ala Lys
1               5                   10

<210> SEQ ID NO 10
<211> LENGTH: 15
<212> TYPE: PRT
<213> ORGANISM: Artificial sequence
<220> FEATURE:
<223> OTHER INFORMATION: Synthetic peptide linker

<400> SEQUENCE: 10

Glu Ala Ala Ala Lys Glu Ala Ala Ala Lys Glu Ala Ala Ala Lys
1               5                   10                  15

<210> SEQ ID NO 11
<211> LENGTH: 20
<212> TYPE: PRT

```
<213> ORGANISM: Artificial sequence
<220> FEATURE:
<223> OTHER INFORMATION: Synthetic peptide linker

<400> SEQUENCE: 11

Glu Ala Ala Ala Lys Glu Ala Ala Ala Lys Glu Ala Ala Ala Lys Glu
1               5                   10                  15

Ala Ala Ala Lys
            20
```

ADP-RIBOSE DETECTION REAGENTS

This application claims benefit of priority to U.S. Provisional Application Ser. No. 62/009,955, filed Jun. 10, 2014, the entire contents of which are hereby incorporated by reference.

This invention was made with government support under grant number DK069710 ("The Role of PARP-1 in Hormone-Regulated Transcription") awarded by the National Institutes of Health/National Institute of Diabetes and Digestive and Kidney Diseases. The government has certain rights in the invention.

BACKGROUND OF THE INVENTION

1. Field

This application relates to diagnostics, assays and detection reagents. In particular, the application describes reagents that are able to detect and distinguish monomers, oligomers, and polymers of ADP-ribose. These reagents are constructed to have the advantageous properties of antibodies with different specificity, selectivity, and affinity than has previously been reported for anti-ADP-ribose antibodies (e.g., the 10H monoclonal antibody).

2. Related Art

ADP-ribose is a naturally-occurring small molecule with a variety of functions. It is commonly found linked to proteins as a post-translational modification. Mono-ADP-ribose (MAR) and poly-ADP-ribose (PAR) transferase enzymes catalyse the transfer (and in the case of PAR transferase enzymes, polymerization) of ADP-ribose units from $NAD^+$, which can be covalently linked glutamate, aspartate, and lysine residues of acceptor proteins. DNA-strand breakage has been considered the main trigger of MAR and PAR synthesis, leading either to repair of the damaged site and cell survival, or cell death, depending on the cellular context and on the intensity of the DNA insult. However, other cellular components (e.g., interacting proteins, nucleosomes, posttranslational modifications, etc.) may also stimulate MAR and PAR synthesis and the size and branching of PAR synthesized under normal conditions is still unclear.

There are at present 17 PARP family members, and it remains to be determined whether all PARP family members can effectively synthesize MAR and/or PAR and, if so, whether they produce structures comparable to that synthesized by the founding member PARP1. Some PARP family members lack conserved residues crucial for polymer elongation and may instead be mono(ADP-ribose) transferases. A detailed biochemical characterization of each PARP family member is necessary to answer the numerous questions that remain regarding PAR synthesis, transfer, function and degradation.

At present, the most widely used (and possibly only available) reagent to investigate ADP-ribose utilization is a monoclonal antibody against poly(ADP-ribose) (PAR). A major drawback of this reagent is that it only detects ADP-ribose in chains of more than ~10 units. In many biological systems, monomers or oligomers of ADP-ribose are the most relevant form.

SUMMARY OF THE INVENTION

Thus, in accordance with the present disclosure, there is provided a fusion protein comprising (a) an Fc domain and (b) a first ADP-ribose binding domain. The Fc domain may be located N-terminal to said first ADP-ribose binding domain, or located C-terminal to said first ADP-ribose binding domain. The Fc domain may be a non-human Fc domain, such as selected from rabbit, mouse, rat, sheep, or goat. The Fc domain may be a human Fc domain, such as from a human IgG, IgA, IgM, IgE or IgD Fc domain.

The first ADP-ribose binding domain may be a mammalian WWE ADP-ribose binding domain, an archeon *A. fulgidus* macrodomain ADP-ribose binding domain, or a mammalian macrodomain ADP-ribose binding domain. The fusion protein may further comprise a hinge region, and/or may further comprise a label or purification tag, such as a poly-His tag, a Strep(II) tag, or an epitope tag. The fusion protein may further comprise a linker disposed between said Fc domain and said first ADP-ribose domain. The fusion protein may comprise a second ADP-ribose binding domain.

The Fc domain may not comprise antigen binding domains and said first ADP-ribose binding domain may be isolated away from polypeptide sequences naturally associated with said ADP-ribose binding domain. The fusion protein may consist essentially of said Fc domain, said first ADP-ribose binding domain, a His(10) tag, a Strep(II) tag, and a linker between said Fc domain and said first ADP-ribose binding domain.

In another embodiment, there is provided an expression vector comprising a nucleic acid segment encoding the fusion protein as defined above, wherein said nucleic acid segment is under the operational control of a promoter. The promoter may be a bacterial promoter or a eukaryotic promoter. The expression vector may further comprise a multiple cloning site positioned adjacent to an Fc domain coding sequence. The expression vector may further comprise a bacterial origin of replication and/or a selectable marker. The expression vector may comprise a LacI gene and an AmpR gene.

In yet another embodiment, there is provided a method of detecting an ADP-ribose-containing molecule comprising contacting a sample suspected or known to contain a first ADP-ribose-containing molecule with a first fusion protein as described above. The first ADP-ribose-containing molecule may comprise an ADP-ribose monomer, an ADP-ribose oligomer, or an ADP-ribose polymer. The method may further comprise contacting said sample with an anti-ADP ribose antibody. The method may further comprise contacting said sample with a second a fusion protein that has a different ADP-ribose-binding specificity as compared to said first fusion protein, and said first and second fusion proteins are differentially detectable.

The first fusion protein may detect ADP-ribose monomers and said second fusion protein may detect ADP-ribose oligomers. The first fusion protein may detect ADP-ribose monomers and said second fusion protein may detect ADP-ribose polymers. The first fusion protein may detect ADP-ribose oligomers and said second fusion protein may detect ADP-ribose polymers. The fusion proteins may be detected via Western blot, ELISA, RIA, immunoprecipitation, immunofluorescent cell staining, FACS or chromatin immunoprecipitation.

In still yet another embodiment, there is provided a method of determining ADP-ribose monomer, oligomer and polymer levels in a cancer cell from a sample comprising (a) contacting a cancer cell from said sample with a first fusion protein comprising (i) an Fc domain and (ii) at least one ADP-ribose binding domain, wherein said first fusion protein recognizes ADP-ribose monomers; (b) contacting said cancer cell with a second fusion protein comprising (i) an Fc domain and (ii) at least one ADP-ribose binding domain, wherein said first fusion protein recognizes ADP-ribose oligomers; (c) contacting said cancer cell with an antibody that recognizes ADP-ribose polymers larger than oligomers; (d) measuring the binding of said first and second fusion proteins and said antibody to said cell, and (e) comparing binding patterns, wherein binding only of said first fusion protein indicates the presence of monomer's, binding of both said first and second fusion proteins indicates the presence of oligomers, and binding of said first and second fusion proteins and said antibody indicates the presence of polymers.

The Fc domain of said first and/or second fusion protein may be located N-terminal to said ADP-ribose binding domain. The Fc domain of said first and/or second fusion protein may be located C-terminal to said ADP-ribose binding domain. The Fc domain of said first and/or second fusion protein may be a non-human Fc domain, such as selected from rabbit, mouse, rat, sheep, or goat. The Fc domain of said first and/or second fusion protein may be a human Fc domain, such as a human IgG, IgA, IgM, IgE or IgD Fc domain. The first and/or second fusion may comprise at least a second ADP-ribose binding domain.

The ADP-ribose binding domain of said first and/or second fusion protein may be a mammalian WWE ADP-ribose binding domain, an archeon *A. fulgidus* macrodomain ADP-ribose binding domain or a mammalian macrodomain ADP-ribose binding domain. The first and/or second fusion protein may further comprises hinge region, and/or may further comprising a label or purification tag, such as a poly-His tag, a Strep(II) tag, or an epitope tag. The first and/or second fusion proteins may further comprise a linker disposed between said Fc domain and said ADP-ribose domain. The Fc domain of said first and/or second fusion protein may not comprise antigen binding domains and said ADP-ribose binding domain may be isolated away from polypeptide sequences naturally associated with said ADP-ribose binding domain. The first and/or second fusion protein may consist essentially of said Fc domain, said ADP-ribose binding domain, a His(10) tag, a Strep(II) tag, and a linker disposed between said Fc domain and said ADP-ribose binding domain.

The cancer cell is a breast cancer cell, a brain cancer cell, a lung cancer cell, a liver cancer cell, a prostate cancer cell, an esophageal cancer cell, a head & neck cancer cell, an ovarian cancer cell, a uterine cancer cell, a testicular cancer cell, a stomach cancer cell, a colon cancer cell, a colorectal cancer cell, a skin cancer cell, a blood cancer cell, nasopharyngeal cancer cell, or a pancreatic cancer cell. The cancer cell may be a recurrent cancer cell, a metastatic cancer cell, a non-metastatic cancer cell and/or a multi-drug resistant cancer cell. The cancer cell may be a human cancer cell. The method may further comprise quantifying the binding of said first fusion protein, said second fusion protein and/or said antibody to determine relative amounts of said monomer, oligomer and polymer.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

FIGS. 1.1-1.5. Schematic representation of recombinant proteins in which natural ADP-ribose binding domains (ARBDs) are fused to mammalian immunoglobulin G (IgG) Fc region. The ARBD-Fc fusion proteins contain the following components fused N-terminally to C-terminally: (FIG. 1.1) a $His_{10}$ tag, which can be used for purification using nickel-affinity chromatography (or related purification methods), (FIG. 1.2) a Strep-tag (synthetic peptide consisting of eight amino acids Trp-Ser-His-Pro-Gln-Phe-Glu-Lys), which can be used for detection or purification, (FIG. 1.3) a natural ADP-ribose binding domain (e.g., WWE(RNF146), Macro(AF1521), Macro(mH2A1.1), Macro3X(PARP14)), (FIG. 1.4) a short linker to accommodate a restriction enzyme site in the plasmid vector, and (FIG. 1.5) an Fc regions from a mammalian IgG (e.g., rabbit, mouse, or human).

FIG. 2. Bacterial plasmids for expressing ADP-Ribose binding domain-Fc fusion proteins. A standard bacterial vector for expressing ADP-Ribose binding domain-Fc fusion proteins containing a DNA sequence cassette with a sequence encoding the key components listed in FIGS. 1.1-1.5 (blue arrow in the schematics at top; red boxed inset at bottom) inserted into a multi-cloning site (MCS) of the vector. The vector also contains promoter driving transcription of the cassette (bent arrow in inset), an antibiotic selectable marker gene (e.g., AmpR), and a bacterial origin of DNA replication (e.g., ORI). One example of a vector containing a MCS, promoter, antibiotic selectable marker gene, and bacterial origin of DNA replication is the pET19b vector, although any vector with such elements could be used as a host for the DNA sequence cassette encoding the ADP-Ribose binding domain-Fc fusion protein.

DESCRIPTION OF ILLUSTRATIVE EMBODIMENTS

Figure 3:
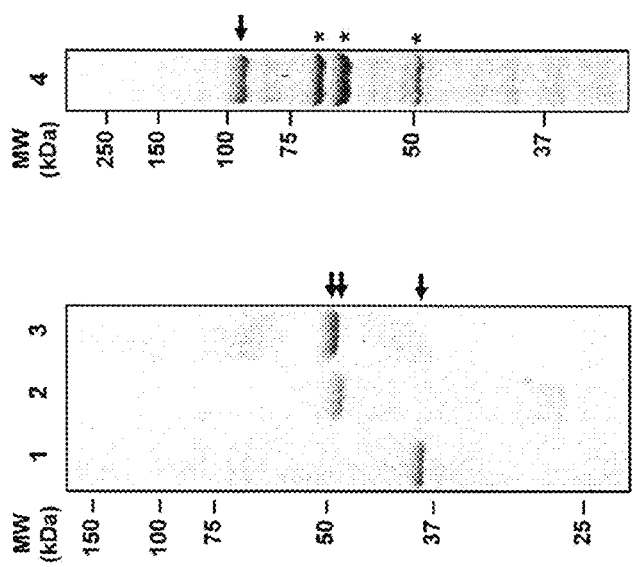
FIG. 3. Analysis of purified ADP-ribose binding domain-Fc fusion proteins by polyacrylamide gel electrophoresis. ARBD-Fc fusion proteins containing the following nature ADP-ribose-binding domains: WWE(RNF146), Macro (AF1521), Macro(mH2A1.1), Macro3X(PARP14), were expressed in *E. coli*, purified under native/denaturing conditions using nickel-NTA affinity chromatography and then analyzed on a 12% (lanes 1-3) or 10% (lane 4) PAGE-SDS gels and stained with Comassie blue stain. The sizes of the marker protein in kilodaltons (kDa) are indicated and the predicted sizes of the purified ARBD-Fc fusion proteins are listed. The extra bands marked with asterisks in lane 4 are common contaminating bacterial proteins, which do not affect the binding of ADP-ribose by Macro3X(PARP14)-Fc and can be removed by further chromatography.

ADP-ribose is a small molecule with a variety of functions. It is commonly found in proteins as a post-translational modification. The inventors have developed four protein-based reagents that can bind monomers, oligomers, and/or polymers of ADP-ribose and, hence, can be used as detection reagents to identify and distinguish these modifications in biological or chemical assays. Each reagent has two main components: an ADP-ribose binding module and an Fc region of an immunoglobulin heavy chain. The latter is a unique aspect of the reagent which confers antibody-like properties on the ADP-ribose binding module, allowing it to be used in all applications where an antibody would be employed (immunoprecipitation, Western blotting, immunofluorescence, etc.). These and other aspects of the disclosure are provided in detail below.

I. ADP-Ribose

A. Structure

Adenosine diphosphate ribose is a diphosphate ester between two ribose sugar units with a terminal adenosine moiety:

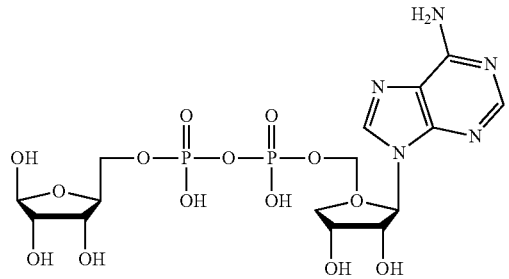

It exists in monomeric, oligomeric (2-10 units), and polymeric (11 to >200 units) forms. The molecules may be found in a free state or linked covalently through the free ribose moiety to proteins via a glutamic acid residue.

B. Function

Poly(ADP-ribosyl)ation modulates protein function by regulating either enzymatic activities or macromolecular interactions with proteins, DNA or RNA. On the other hand, PAR molecules can also regulate protein activity and function through non-covalent binding. This is illustrated by the growing list of protein-protein, protein-DNA and protein-RNA interactions that either require or are prevented by PAR. A number of modules (specific amino acid structures that form distinct structures) in proteins have been found to bind various forms of ADP-ribose. This include: (1) a somewhat conserved 20 amino-acid PAR-binding motif (PBM), which was initially established from the analysis of several DNA-repair and checkpoint proteins (Pleschke et al., 2000); (2) some macro domains, such as those found in macroH2A1.1, PARP9, or in a viral protein from the SARS coronavirus 3 (3) a $C_2H_2$ zinc-finger, known as the PBZ; and (4) the WWE domain, which have all been shown to bind to MAR or PAR in vitro (Ahel et al., 2008; Egloff et al., 2006; Karras et al., 2005). In some cases, a single protein target can bind to PAR non-covalently and also be an acceptor for poly(ADP-ribosyl)ation. These processes can involve such divergent actions as recruitment to a site were PAR is produced, and modification of the activity of the recruited protein. Whether the effect of PAR is due to steric hindrance or to electrostatic repulsion generated by the negatively-charged polymers is still unknown. Differences in the length and branching of PAR may add another level of regulation allowing different functional outcomes (Fahrer et al., 2007).

Among the other roles proposed for PAR is as a local supply of ATP molecules, important in conditions of ATP shortage. PARP1 activation in response to DNA breaks could supply the ATP necessary for ligation, the final step of single-strand break repair (SSBR). Converting PAR into ATP requires pyrophosphate, which occurs during DNA-repair synthesis (Petermann et al., 2003). AMPK, which is activated when the ATP concentration is limiting, phosphorylates PARP1, thereby enhancing its automodification (Walker et al., 2006).

A role for PAR and/or ADP-ribose as a signaling molecule is another possible role. Indeed, an essential function for PAR is during initiation of caspase-independent cell-death pathway. In addition, ADP-ribose acts as a second messenger that activates the TRPM2 channel, allowing $Ca^{2+}$ influx in response to oxidative stress. A direct involvement of PARP1/PARG in producing these ADP-ribose molecules was recently revealed (Buelow et al., 2008).

II. Fusion Proteins

A. Structure

The present disclosure contemplates the design, production and use of various fusion proteins. The contemplated molecules will have at least two elements: an ADP-ribose binding moiety, and at least a portion of an immunoglobulin Fc sequence, and may optionally include a linker disposed there between. Each of these elements is described in greater detail below.

1. ADP Ribose Binding Domains

The fusion proteins described herein make use of four naturally occurring ADP-ribose binding domains, specified as follows:
1) WWE(RNF146)=RNF146 WWE domain from *Homo sapiens* (Human)
2) Macro(AF1521)=AF1521 macrodomain from *Archaeoglobus fulgidus* (Archeabacterium)
3) Macro(mH2A1.1)=MacroH2A1.1 macrodomain from *Homo sapiens* (Human)
4) Macro3X(PARP14)=Macrodomains 1 through 3 of PARP14 from *Homo sapiens* (Human)

Other naturally-occurring or synthetic ADP-ribose binding domains could also be used to the same effect.

RNF146 WWE Domain.

One molecule containing a suitable ADP-ribose binding domain is mammalian RNF146, which contains a WWE domain that binds to both poly-ADP-ribose and oligo-ADP-ribose, but does not bind mono-ADP-ribose. RNF146 is an E3 ubiquitin-protein ligase that specifically binds poly-ADP-ribosylated (PARylated) proteins and mediates their ubiquitination and subsequent degradation. It may also regulate many important biological processes, such as cell survival and DNA damage response. It acts as an activator of the Wnt signaling pathway by mediating the ubiquitination of PARylated AXIN1 and AXIN2, 2 key components of the beta-catenin destruction complex, and acts in cooperation with tankyrase proteins (TNKS and TNKS2), which mediate PARylation of target proteins AXIN1, AXIN2, BLZF1, CASC3, TNKS and TNKS2. It recognizes and binds tankyrase-dependent PARylated proteins via its WWE domain and mediates their ubiquitination, leading to their degradation. It is the WWE domain that can be used in accordance with the present disclosure. The amino acid sequence of the RNF146 WWE domain-Fc fusion is as follows (single letter code for the amino acids):

MGHHHHHHHHHHSSGHIDDDDKHMWSHPQFEKGSSGNGEYAWYYEGRNGW

WQYDERTSRELEDAFSKGKKNTEMLIAGFLYVADLENMVQYRRNEHGRRR

KIKRDIIDIPKKGVAGLRLDGSTGSSSKPTCPPPELLGGPSVFIFPPKPK

DTLMISRTPEVTCVVVDVSQDDPEVQFTWYINNEQVRTARPPLREQQFNS

TIRVVSTLPIAHQDWLRGKEFKCKVHNKALPAPIEKTISKARGQPLEPKV

YTMGPPREELSSRSVSLTCMINGFYPSDISVEWEKNGKAEDNYKTTPAVL

DSDGSYFLYSKLSVPTSEWQRGDVFTCSVMHEALHNHYTQKSISRSPGK
(SEQ ID NO: 1; NP_001229773.1 and NM_001242844.1; Key: underline = $His_{10}$ tag; double-underline = StrepTag core sequence; italicized = RNF146 WWE domain; bold = rabbit Fc)

AF1521 Macrodomain.

The macrodomain from the archeon *Archaeoglobus fulgidus* AF1521 protein is another suitable ADP-ribose binding domain for use in accordance with the present disclosure. This molecule includes a stand-alone macro domain having a mixed alpha/beta-fold that closely resembles the N-terminal DNA binding domain of the *Escherichia coli* leucine aminopeptidase PepA. The structure also shows some similarity to members of the P-loop family of nucleotide hydrolases. The AF1521 macrodomain binds mono, oligo, and poly-ADP-ribose. The amino acid sequence of the AF1521 macrodomain-Fc fusion is as follows (single letter code for the amino acids):

MGHHHHHHHHHHSSGHIDDDDKHMWSHPQFEKMERRTLIMEVLFEAKVGD

ITLKLAQGDITQYPAKAIVNAANKRLEHGGGVAYAIAKACAGDAGLYTEI

SKKAMREQFGRDYIDHGEVVVTPAMNLEERGIKYVFHTVGPICSGMWSEE

LKEKLYKAFLGPLEKAEEMGVESIAFPAVSAGIYGCDLEKVVETFLEAVK

NFKGSAVKEVALVTYDRKSAEVALKVFERSLGSTGSSSKPTCPPPELLGG

PSVFIFPPKPKDTLMISRTPEVTCVVVDVSQDDPEVQFTWYINNEQVRTA

RPPLREQQFNSTIRVVSTIRVVSTLPIAHQDWLRGKEFKCKVHNKALPAP

IEKTISKARGQPLEPKVYTMGPPREELSSRSVSLTCMINGFYPSDISVEW

EKNGKAEDNYKTTPAVLDSDGSYFLYSKLSVPTSEWQRGDVFTCSVMHEA

LHNHYTQKSISRSPGK
(SEQ ID NO: 2; NP_070350.1 and NC_000917.1; Key: underline = $His_{10}$ tag; double-underline = StrepTag core sequence; italicized = AF1521 macrodomain; bold = rabbit Fc)

MacroH2A1.1 Macrodomain.

The macrodomain from the mammalian macroH2A1.1 protein is another suitable ADP-ribose binding domain for use in accordance with the present disclosure. This protein has a single macrodomain located carboxy-terminal to a histone H2A domain. MacroH2A is an unusual histone H2A variant that has an extensive C-terminal tail that comprises approximately two thirds of the protein. While the macrodomain in the macroH2A1.1 isoform binds ADP-ribose, the macrodomains in the 1.2 and 2 isoforms do not. The macroH2A1.1 macrodomain binds mono and poly-ADP-ribose, but has low affinity for oligo-ADP-ribose. The amino acid sequence of the macroH2A1.1 macrodomain-Fc fusion is as follows (single letter code for the amino acids):

MGHHHHHHHHHHSSGHIDDDDKHMGEVSKAASADSTTEGTPADGETVLST

KSLFLGQKLQVVQADIASIDSDAVVHPTNTDFYIGGEVGNTLEKKGGKEF

-continued

VEAVLELRKKNGPLEVAGAAVSAGHGLPAKFVIHCNSPVWGADKCEELLE

KTVKNCLALADDKKLKSIAFPSIGSGRNGFPKQTAAQLILKAISSYFVST

MSSSIKTVYFVLFDSESIGIYVQEMAKLDANLDGSTGSSSKPTCPPPELL

GGPSVFIFPPKPKDTLMISRTPEVTCVVVDVSQDDPEVQFTWYINNEQVR

TARPPLREQQFNSTIRVVSTLPIAHQDWLRGKEFKCKVHNKALPAPIEKT

ISKARGQPLEPKVYTMGPPREELSSRSVSLTCMINGFYPSDISVEWEKNG

KAEDNYKTTPAVLDSDGSYFLYSKLSVPTSEWQRGDVFTCSVMHEALHNH

YTQKSISRSPGK
(SEQ ID NO: 3; NP_613075.1 and NM_138609.2; Key:
underline = His$_{10}$ tag; italicized = macroH2A1.1
macrodomain; bold = rabbit Fc)

PARP14 Triple Macrodomain Cassette.

The macrodomains from the mammalian PARP14 protein provide another suitable ADP-ribose binding domain for use in accordance with the present disclosure. PARP14 has a set of three adjacent macrodomains (1, 2, and 3) forming a cassette that binds mono-ADP-ribose, but has low affinity for oligo- or poly-ADP-ribose, likely because they bind the terminal ADP-ribose units and contact features in the target protein as well. The PARP14 macrodomains bind ADP-ribose alone or when linked in tandem, although the affinity is higher for the tandem arrangement. The amino acid sequence of the PARP14 three macrodomain cassette-Fc fusion is as follows (single letter code for the amino acids):

MG<u>HHHHHHHHHH</u>SSGHIDDDDKHMTDKPGAKQFFQDKARFYQSEIKRLFG

CYIELQENEVMKEGGSPAGQKCFSRTVLAPGVVLIVQQGDLARLPVDVVV

NASNEDLKHYGGLAAALSKAAGPELQADCDQIVKREGRLLPGNATISKAG

KLPYHHVIHAVGPRWSGYEAPRCVYLLRRAVQLSLCLAEKYKYRSIAIPA

ISSGVFGFPLGRCVETIVSAIKENFQFKKDGHCLKEIYLVDVSEKTVEAF

AEAVKTVFKATLPDTAAPPGLPPAAAGPGKTSWEKGSLVSPGGLQMLLVK

EGVQNAKTDVVVNSVPLDLVLSRGPLSKSLLEKAGPELQEELDTVGQGVA

VSMGTVLKTSSWNLDCRYVLHVVAPEWRNGSTSSLKIMEDIIRECMEITE

SLSLKSIAFPAIGTGNLGFPKNIFAELIISEVFKFSSKNQLKTLQEVHFL

LHPSDHENIQAFSDEFARRANGNLVSDKIPKAKDTQGFYGTVSSPDSGVY

EMKIGSIIFQVASGDITKEEADVIVNSTSNSFNLKAGVSKAILECAGQNV

ERECSQQAQQRKNDYIITGGGFLRCKNIIHVIGGNDVKSSVSSVLQECEK

KNYSSICLPAIGTGNAKQHPDKVAEAIIDAIEDFVQKGSAQSVKKVKVVI

FLPQVLDVFYANMKKREGLDGSTGSSSKPTCPPPELLGGPSVFIFPPKPK

DTLMISRTPEVTCVVVDVSQDDPEVQFTWYINNEQVRTARPPLREQQFNS

TIRVVSTLPIAHQDWLRGKEFKCKVHNKALPAPIEKTISKARGQPLEPKV

YTMGPPREELSSRSVSLTCMINGFYPSDISVEWEKNGKAEDNYKTTPAVL

DSDGSYFLYSKLSVPTSEWQRGDVFTCSVMHEALHNHYTQKSISRSPGK
(SEQ ID NO: 4; NP_060024.2 and NM_017554.2;
Key: underline = His$_{10}$ tag; italicized =
PARP14 macrodomains 1 - 3; bold = rabbit Fc)

Other suitable sources for an ADP-ribose binding domain include the non-structural proteins of several types of ssRNA viruses such as NSP2 from alpha viruses (P03317). It is also found on its own in a family of proteins from bacteria (P75918), archaebacteria (O59182) and eukaryotes (Q17432), suggesting that it is involved in an important and ubiquitous cellular process. Consistently, distinct human macro domains retain their ability to bind variations of ADP-ribose. The macro domains of the MACROD1 and MACROD2 O-acetyl-ADP-ribose deacetylases are also suitable sources of ADP-ribose binding domains and would presumably retain selective activity toward non-polymeric versions of ADP-ribose.

Other mono- and poly-ADP-ribose binding proteins such as those containing PAR-binding motifs (PBMs) and PAR-binding zinc fingers (PBZs) may also provide sequences that can be used as ADP-ribose recognition modules.

In some embodiments, the fusion proteins may contain more than one ADP-ribose binding domain. These multiple ADP-ribose binding domains will advantageously be of the same sequence, although in certain embodiments it is conceivable that one can use two or more distinct ADP-ribose binding domains, such as the case with the triple macrodomain cassette from PARP14. Such combinations may improve affinity or alter specificity.

2. Fc Domains

The Fc (fragment, crystallizable) region of immunoglobulin interacts with the Fc receptor on certain cells. In many biological applications using immunological methods, the Fc region is the target of molecular probes, affinity reagents, and detection reagents. Thus, the presence of an Fc region can link specific affinity detection with a whole host of immunological tools. The constant region is identical in all antibodies of the same isotype, but differs in antibodies of different isotypes. There are five types of mammalian Ig heavy chains, denoted by the Greek letters: α, δ, ε, γ, and μ, the constant regions of which dictate the structure of the Fc. Distinct heavy chains differ in size and composition; α and γ contain approximately 450 amino acids, while μ and ε have approximately 550 amino acids. Heavy chains γ, α and δ have a constant region composed of three tandem (in a line) Ig domains, and a hinge region for added flexibility; heavy chains μ and ε have a constant region composed of four immunoglobulin domains.

Fc regions from a variety of different species may be employed, including human, monkey, gibbon, guinea pig, hamster, rabbit, mouse, rat, and sheep. In some embodiments, it may be advantageous to employ two different fusions, each having an Fc region from a different species so as to be able to differentiate between the two molecules while being used simultaneously.

3. Linkers

Peptide linkers (i.e., short sequences of amino acids that join two polypeptide domains in a contiguous sequence) or cross-linking agents (chemicals that can covalently two polypeptide domains) may be used to fuse the ADP-ribose binding segment to the constant region (Fc) of human or mouse IgG1 sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

This chimeric proteins can be constructed by that addition of flexible peptide linkers such as (GGGGS)$_n$ where n=2-5. Moreover helical linkers such as (EAAAK)$_n$ where n=2-6 can also be used to provide proper conformation to the chimeric protein. The various sequences of the flexible linkers can be:

```
                                            (SEQ ID NO: 5)
    GGGGS GGGGS (SEQ ID NO: 6)
    GGGGS GGGGS GGGGS (SEQ ID NO: 7)
    GGGGS GGGGS GGGGS GGGGS (SEQ ID NO: 8)
    GGGGS GGGGS GGGGS GGGGS GGGGS
```

The various sequences of the helical linkers can be:

```
                                            (SEQ ID NO: 9)
    EAAAK EAAAK (SEQ ID NO: 10)
    EAAAK EAAAK EAAAK (SEQ ID NO: 11)
    EAAAK EAAAK EAAAK EAAAK
```

Other combinations are contemplated as well.

4. Non-Natural Modifications

The present disclosure may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

B. Chemical Synthesis

It may be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Recombinant Production

In addition to chemical synthesis, the fusion proteins of the present disclosure may, for example, advantageously be produced by recombinant methods using the vectors described in FIG. 2 (or related derivatives). Nucleic acids according to the present disclosure will encode the fusion proteins, and optionally further include sequences. As used in this application, the term "a nucleic acid encoding a fusion protein" refers to a nucleic acid molecule that has been isolated free of total cellular nucleic acid.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The DNA segments of the present disclosure include those encoding biologically functional equivalent proteins and peptides of the sequences described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Within certain embodiments, expression vectors are employed to express a fusion protein in order to produce and isolate the polypeptide expressed therefrom. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control" and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively controls the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

2. IRES

In certain embodiments of the disclosure, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference).

5. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670, 488). The various viral vectors described below, present specific advantages and disadvantages, depending on the particular gene-therapeutic application.

Adenoviral Vectors.

In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present disclosure comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a $\psi$ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The $\psi$ sequence is required for the packaging of the adenoviral genome.

A common approach for generating adenoviruses for use as a gene transfer vectors is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present disclosure it may be convenient to introduce the transforming construct at the position from which the E1-coding sequences have been removed. However, the position of insertion of the construct within the adenovirus sequences is not critical to the disclosure. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. No. 5,670,488; U.S. Pat. No. 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1996) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the disclosure. The adenovirus may be of any of the 42 different known serotypes and/or subgroups A-F. Adenovirus type 5 of subgroup C is the preferred starting material in order to obtain the conditional replication-defective adenovirus vector for use in the present disclosure. This is because adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Adenovirus growth and manipulation is known to those of skill in the art, and exhibits broad host range in vitro and in vivo (U.S. Pat. No. 5,670,488; U.S. Pat. No. 5,932,210; U.S. Pat. No. 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors Retroviral Vectors.

In certain embodiments of the disclosure, the uses of retroviruses for gene delivery are contemplated. Retroviruses are RNA viruses comprising an RNA genome. When a host cell is infected by a retrovirus, the genomic RNA is reverse transcribed into a DNA intermediate, which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present disclosure may be genetically modified in such a way that some of the structural, infectious genes of the native virus have been removed and replaced instead with a nucleic acid sequence to be delivered to a target cell (U.S. Pat. No. 5,858,744; U.S. Pat. No. 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present disclosure are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. No. 5,955,331; U.S. Pat. No. 5,888,502, each specifically incorporated herein by reference). Nolan et al. describe the production of stable high titer, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present disclosure (U.S. Pat. No. 5,955,331).

Herpesviral Vectors.

Herpes simplex virus (HSV) type I and type II contain a double-stranded, linear DNA genome of approximately 150 kb, encoding 70-80 genes. Wild-type HSV is able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miyatake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernible phases or kinetic classes. These phases of genes are referred to as the Immediate Early (IE) or α genes, Early (E) or β genes and Late (L) or γ genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. No. 5,879,934; U.S. Pat. No. 5,851,826, each specifically incorporated herein by reference in its entirety). One IE protein, ICP4, also known as α4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors.

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions, which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods that employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this disclosure, into that packaging cell yields a producer cell, which releases infectious viral particles carrying the foreign gene of interest. The env preferably is an amphotropic envelope protein, which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene, which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells, which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present disclosure, one may graft or transplant cells infected with the recombinant lentivirus ex vivo, or infect cells in vivo.

Other Viral Vectors.

The development and utility of viral vectors for gene delivery is constantly improving and evolving. Other viral vectors such as poxvirus; e.g., vaccinia virus (Gnant et al., 1999a; Gnant et al., 1999b), alpha virus; e.g., sindbis virus, Semliki forest virus (Lundstrom, 1999), reovirus (Coffey et al., 1998) and influenza A virus (Neumann et al., 1999) are contemplated for use in the present disclosure and may be selected according to the requisite properties of the target system.

In certain embodiments, vaccinia viral vectors are contemplated for use in the present disclosure. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999a), inner ear (Derby et al., 1999), glioma cells, e.g., p53 (Timiryasova et al., 1999) and various mammalian cells, e.g., $P_{450}$ (U.S. Pat. No. 5,506,138). The preparation, growth and manipulation of vaccinia viruses are described in U.S. Pat. No. 5,849,304 and U.S. Pat. No. 5,506,138 (each specifically incorporated herein by reference).

In other embodiments, sindbis viral vectors are contemplated for use in gene delivery. Sindbis virus is a species of the alphavirus genus (Garoff and Li, 1998), which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, it has a wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors.

Chimeric or hybrid viral vectors are being developed for use in therapeutic gene delivery and are contemplated for use in the present disclosure. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

10. Non-Viral Transformation

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat.

No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner.

11. Expression Systems

Numerous expression systems exist that comprise at least a part or all of the compositions discussed above. Prokaryote- and/or eukaryote-based systems can be employed for use with the present disclosure to produce nucleic acid sequences, or their cognate polypeptides, proteins and peptides. Many such systems are commercially and widely available.

An exemplified expression system is an RNA polymerase expression system that is highly selective for bacteriophage T7 RNA polymerase. The initial system involved two different methods of maintaining T7 RNA polymerase into the cell—in one method, a lambda bacteriophage was used to insert the gene which codes for T7 RNA polymerase, and in the other, the gene for T7 RNA polymerase was inserted into the host chromosome. This expression system has become known as the pET Expression System, and is now widely used because of its ability to mass-produce proteins, the specificity involved in the T7 promoter which only binds T7 RNA polymerase, and also the design of the system which allows for the easy manipulation of how much of the desired protein is expressed and when that expression occurs.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MaxBac® 2.0 from Invitrogen® and BacPack™ Baculovirus Expression System From Clontech®.

Other examples of expression systems include Stratagene®'s Complete Control™ Inducible Mammalian Expression System, which involves a synthetic ecdysone-inducible receptor, or its pET Expression System, an E. coli expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr that confers sensitivity to methotrexate; gpt, that confers resistance to myeophenolic acid; neo, that confers resistance to the aminoglycoside G418; and hygro, that confers resistance to hygromycin.

D. Design, Variants and Analogs

Variants of the peptide/polypeptide sequences discussed above may be employed. For example, certain non-natural amino acids that satisfy the structural constraints of the ligand traps may be substituted without a loss, and perhaps with an improvement in, biological function. In addition, the present inventors also contemplate that structurally similar compounds may be formulated to mimic the key portions of peptide or polypeptides of the present disclosure. Such compounds, which may be termed peptidomimetics, may be used in the same manner as the peptides of the disclosure and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the disclosure also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., PCT/US99/11913, the disclosure of which is incorporated herein by reference in its entirety). Other molecular modeling techniques may also be employed in accordance with this disclosure (e.g., Cohen et al., 1990; Navia et al., 1992; the disclosures of which are incorporated herein by reference in their entirety). All these methods produce data that are amenable to computer analysis. Other spectroscopic methods that can also be useful in the method of the disclosure, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source, and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from U.S. Patent Application No. 2005/0015232, U.S. Pat. No. 6,093,573, PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety E. Purification of Proteins It may be desirable to purify the fusion polypeptides according to the present disclosure. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean, N-acetyl glucosaminyl binds to lectins from wheat germ; D-galactosamine has been used in obtaining lectins from clams and L-fuctose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

Polyhistidine-tags are often used for affinity purification of polyhistidine-tagged recombinant proteins expressed in *Escherichia coli* and other prokaryotic expression systems. Bacterial cells are harvested via centrifugation and the resulting cell pellet lysed either by physical means or by means of detergents and enzymes such as lysozyme. At this stage raw lysate contains the recombinant protein among many other proteins originating from the bacterial host. This mixture is incubated with an affinity resin containing bound bivalent nickel or cobalt ions, which are available commercially in different varieties. Nickel and cobalt have similar properties and as they are adjacent period 4 transition metals (v. iron triad). These resins are generally sepharose/agarose functionalised with a chelator, such as iminodiacetic acid (Ni-IDA) and nitrilotriacetic acid (Ni-NTA) for nickel and carboxylmethylaspartate (Co-CMA) for cobalt, which the polyhistidine-tag binds with micromolar affinity. The resin is then washed with phosphate buffer to remove proteins that do not specifically interact with the cobalt or nickel ion. With Ni-based methods, washing efficiency can be improved by the addition of 20 mM imidazole (proteins are usually eluted with 150-300 mM imidazole). Generally nickel-based resins have higher binding capacity, while cobalt-based resins offer the highest purity. The purity and amount of protein can be assessed by SDS-PAGE and Western blotting.

Affinity purification using a polyhistidine-tag usually results in relatively pure protein when the recombinant protein is expressed in prokaryotic organisms. Depending on downstream applications, including the purification of protein complexes to study protein interactions, purification from higher organisms such as yeasts or other eukaryotes may require a tandem affinity purification using two tags to yield higher purity. Alternatively, single-step purification using immobilized cobalt ions rather than nickel ions generally yields a substantial increase in purity and requires lower imidazole concentrations for elution of the his-tagged protein.

Polyhistidine-tagging is the option of choice for purifying recombinant proteins in denaturing conditions because its mode of action is dependent only on the primary structure of proteins. Generally for this sort of a technique, histidine binding is titrated using pH instead of imidazole binding—at a high pH, histidine binds to nickel or cobalt, but at low pH (~6 for cobalt and ~4 for nickel), histidine becomes protonated and is competed off of the metal ion. Compare this to antibody purification and GST purification, a prerequisite to which is the proper (native) folding of proteins involved.

Polyhistidine-tag columns retain several well known proteins as impurities. One of them is FKBP-type peptidyl prolyl isomerase, which appears around 25 kDa (SlyD). Impurities are generally eliminated using a secondary chromatographic technique, or by expressing the recombinant protein in a SlyD-deficient *E. coli* strain. Alternatively cobalt-based resins do not bind SlyD from *E. coli* and can be used for a single-step purification.

IV. Assays

A. Protein Conjugates

Fusion proteins according to the present disclosure may be linked to at least one agent to form a protein conjugate. In order to increase the efficacy of fusion molecules as diagnostic agents, it is conventional to link or covalently bind or complex at least one desired molecule or moiety. Such a molecule or moiety may be, but is not limited to, at least one reporter or detectable molecule. Non-limiting examples of reporter molecules which have been conjugated to proteins include enzymes, radiolabels, haptens, fluorescent labels, phosphorescent molecules, chemiluminescent molecules, chromophores, photoaffinity molecules, colored particles or ligands, such as biotin.

Protein conjugates are generally preferred for use as diagnostic agents. Protein diagnostics generally fall within two classes, those for use in in vitro diagnostics, such as in a variety of immunoassays, and those for use in vivo diagnostic protocols, generally known as "protein-directed imaging." Many appropriate imaging agents are known in the art, as are methods for their attachment to targeting proteins (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled proteins may be produced according to well-known methods in the art. For instance, proteins can be iodinated by contact with sodium and/or potassium iodide and a chemical oxidizing agent such as sodium hypochlorite, or an enzymatic oxidizing agent, such as lactoperoxidase. Proteins may be labeled with technetium$^{99m}$ by ligand exchange process, for example, by reducing pertechnate with stannous solution, chelating the reduced technetium onto a Sephadex column and applying the protein to this column. Alternatively, direct labeling techniques may be used, e.g., by incubating pertechnate, a reducing agent such as SNCl$_2$, a buffer solution such as sodium-potassium phthalate solution, and the protein. Intermediary functional groups which are often used to bind radioisotopes which exist as metallic ions to proteins are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of conjugate contemplated is one intended primarily for use in vitro, where the protein is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and described, for example, in U.S. Pat. Nos. 3,817,837, 3,850,752, 3,939,350, 3,996,345, 4,277,437, 4,275,149 and 4,366,241.

Molecules containing azido groups may also be used to form covalent bonds to proteins through reactive nitrene intermediates that are generated by low intensity ultraviolet light. In particular, 2- and 8-azido analogues of purine nucleotides have been used as site-directed photoprobes to identify nucleotide binding proteins in crude cell extracts. The 2- and 8-azido nucleotides have also been used to map nucleotide binding domains of purified proteins and may be used as protein binding agents.

Other attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the protein. Proteins may also be reacted with an enzyme in the presence of a coupling agent such as glutaraldehyde or periodate. Conjugates with fluorescein markers are prepared in the presence of these coupling agents or by reaction with an isothiocyanate.

In other embodiments, derivatization of immunoglobulins by selectively introducing sulfhydryl groups in the Fc region of an immunoglobulin, using reaction conditions that do not alter the antibody combining site are contemplated. Conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

B. PARP Immobilization Methods

In other embodiments, protein assays include the use of clickable NAD analogs. These clickable NAD analogs contain an azide or an alkyne as a part of the adenosine or the ribose and are attached to the target protein via the activity of a PARP protein. Once attached to the protein or protein conjugate, these compounds can then be subjected to click conditions to covalently link the modified target protein to a group such as biotin. The biotinylated protein or protein conjugate is then exposed to a solid support coated with avidin which immobilizes the protein or protein conjugate. Once the protein has been immobilized, the protein can be isolated and subjected to identification techniques such as PCR or deep sequencing if desired. This method may also be used to identify other molecules to which the protein is bound such as nucleic acids bound to a chromatin molecule. Cross-linking may be used in such instances to prevent the disassembly complex between the protein and the other molecule.

C. Immunodetection Methods

Also provided are detection methods for binding, purifying, removing, quantifying and otherwise generally detecting ADP-ribose and its associated proteins. Some methods that can be adapted for using with the fusion proteins of the present disclosure include enzyme linked immunosorbent assay (ELISA), radioimmunoassay (RIA), immunoradiometric assay, fluoroimmunoassay, chemiluminescent assay, bioluminescent assay, and Western blot to mention a few. In general, immunobinding methods can be used with the present fusions proteins and will include obtaining a sample and contacting the sample with a fusion protein in accordance with embodiments discussed herein, as the case may be, under conditions effective to allow the formation of complexes.

Contacting the chosen biological sample with the fusion protein under effective conditions and for a period of time sufficient to allow the formation of complexes is generally a matter of simply adding the fusion protein composition to the sample and incubating the mixture for a period of time long enough for the fusion protein to form complexes with, i.e., to bind to ADP-ribose. After this time, the sample-fusion protein composition, such as a tissue section, ELISA plate, dot blot or Western blot, will generally be washed to remove any non-specifically bound fusion protein species, allowing only those fusion protein specifically bound within the primary complexes to be detected.

In general, the detection of complex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The fusion protein employed in the detection may itself be linked to a detectable label, wherein one would then simply detect this label, thereby allowing the amount of the primary complexes in the composition to be determined. Alternatively, the first fusion protein that becomes bound within the primary complexes may be detected by means of a second binding ligand that has binding affinity for the fusion protein. In these cases, the second binding ligand may be linked to a detectable label. The second binding ligand is itself often an antibody, which may thus be termed a "secondary" agent. The primary complexes are contacted with the labeled, secondary binding ligand, or antibody, under effective conditions and for a period of time sufficient to allow the formation of secondary complexes. The secondary complexes are then generally washed to remove any non-specifically bound labeled secondary antibodies or ligands, and the remaining label in the secondary complex is then detected.

Further methods include the detection of primary complexes by a two step approach. A second binding ligand, such as a antibody that has binding affinity for the fusion protein, is used to form secondary complexes, as described above. After washing, the secondary complexes are contacted with a third binding ligand or antibody that has binding affinity for the second antibody, again under effective conditions and for a period of time sufficient to allow the formation of complexes (tertiary complexes). The third ligand or antibody is linked to a detectable label, allowing detection of the tertiary complexes thus formed. This system may provide for signal amplification if this is desired.

Another known method of immunodetection takes advantage of the immune-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule. This method could be adapted to utilize fusion proteins according to the present disclosure rather than antibodies.

The follow sections describe immunoassays that can be utilized by substituting the antigen-specific antibodies with fusion proteins according to the present disclosure.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the samples suspected of containing the ADP-ribose are immobilized onto the well surface and then contacted with the fusion protein. After binding and washing to remove non-specifically bound immune complexes, the bound fusion proteins are detected. Where the initial fusion proteins are linked to a detectable label, the complexes may be detected directly. Again, the complexes may be detected using a second antibody that has binding affinity for the Fc region of the fusion protein, with the antibody being linked to a detectable label.

Irrespective of the format employed, ELISAs have certain features in common, such as coating, incubating and binding, washing to remove non-specifically bound species, and detecting the bound complexes. These are described below.

In coating a plate with either antigen or fusion protein, one will generally incubate the wells of the plate with a solution of the antigen or fusion protein, either overnight or for a specified period of hours. The wells of the plate will then be washed to remove incompletely adsorbed material. Any remaining available surfaces of the wells are then "coated" with a nonspecific protein. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a fusion protein to the well, coating with a non-reactive material to reduce background, and washing to remove unbound material, the immobilizing surface is contacted with the biological sample to be tested under conditions effective to allow complex formation. Detection of the complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C., or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilise proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled fusion protein, or unlabeled fusion protein followed by indirect detection using labeled protein A or secondary labeled antibodies binding to the Fc region of the primary antibodies.

3. Immunohistochemistry

The fusion proteins may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art. This may be particularly useful in the examination of cancer specimens, or specimens suspected of containing cancerous cells/tissues.

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. FACS

In one embodiment of the disclosure, fluorescence activated cell sorting (FACS) screening or other automated flow cytometric techniques may be used for the efficient sorting of cell. Instruments for carrying out flow cytometry are known to those of skill in the art and are commercially available to the public. Examples of such instruments include FACS Star Plus, FACScan and FACSort instruments from Becton Dickinson (Foster City, Calif.), Epics C from Coulter Epics Division (Hialeah, Fla.) and MOFLO® from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation, but in the present application the fusion proteins would be used rather than antibodies.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

D. Detection Kits

In still further embodiments, there are immunodetection kits for use with the immunodetection methods described above. The immunodetection kits will thus comprise, in suitable container means, a fusion protein according to the present disclosure, and optionally a reagent that permits detection of the fusion protein.

In certain embodiments, the fusion protein may be pre-bound to a solid support, such as a column matrix and/or well of a microtiter plate. The immunodetection reagents of the kit may take any one of a variety of forms, including those detectable labels that are associated with or linked to the given fusion protein. Detectable labels that are associated with or attached to a secondary binding ligand are also contemplated. Exemplary secondary ligands are antibodies that have binding affinity for the Fc region of the fusion protein.

Further suitable immunodetection reagents for use in the present kits include the two-component reagent that comprises an antibody that has binding affinity for the Fc portion of the fusion, along with a second antibody that has binding affinity for the first antibody, the second antibody being linked to a detectable label. As noted above, a number of exemplary labels are known in the art and all such labels may be employed in connection with embodiments discussed herein.

The kits may further comprise a suitably aliquoted composition of ADP-ribose monomer, oligomer or polymer, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

V. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Methods

Cloning and Molecular Biology.

cDNA was generated from Trizol extracted cellular RNA originating from 293T cells or 3T3-L1 cells by using a commercially available hi-fidelity reverse transcriptase, Superscript III (Invitrogen), as described by the manufacturer.

ARBD-Fc Fusion Proteins: The DNA sequences encoding RNF146 WWE, and AF1521, MacroH2A1.1, and PARP14 macrodomains were amplified from the cDNA by Polymerase Chain Reaction (PCR) with a 5'-terminal NdeI site, 3'-terminal SalI site. The Rabbit Fc region of Immunoglobulin G (IgG) was synthesized by IDT as three DNA sequence blocks. One of the above ARBD amplicons and the three DNA sequence blocks encoding the rabbit Fc region were combined at equimolar concentrations and amplified into a contiguous linear DNA fragment using PCR with 5' ARBD forward primers and 3' Fc reverse primers. The amplified DNA cassette was cloned into pET19b (Novagen) using NdeI and BamHI sites within the MCS of the plasmid. All constructs were confirmed by sequencing.

PARP1 and PARP3: PARP1 (human; 293T as a source) and PARP3 (mouse; 3T3-L1 as a source) were amplified from high quality cDNA, made as described above, using Polymerase Chain Reaction (PCR) with Phusion DNA polymerase (NEB). A start codon and FLAG tag coding sequence were integrated 5' of the ORFs of PARP1 and PARP3 through primer design and cloned into the multiple cloning site of the pFastBac1 plasmid (Invitrogen). pFastBac1 with flag tagged PARP1 or PARP3 were recombined into a bacmid in *Escherichia coli* strain DH10bac using the Bac-to-Bac protocol, as described by manufacturer (Invitrogen). Clones passing two independent white/blue screens were inoculated into LB supplemented with 7 µg per milliliter Gentamicin, 50 µg per milliliter Kanamycin, and 10 µg per milliliter Tetracycline with overnight growth at 37° C. Bacmids were isolated from bacteria for transfection into Sf9 culture using sodium hydroxide/potassium acetate lysis and isopropanol precipitation of nucleic acids.

Protein Expression:

The recombinant ARBD-Fc fusions, PARP1, and PARP3 were expressed as described below.

ARBD-Fc Fusion Proteins: The pET19b-ARBD-Fc expression vectors were individually transformed into separate chemically-competent *Escherichia coli* strain BL21 (DE3) cells using a heat shock approach. The transformed cells were inoculated into 5 ml of Luria Broth supplemented with 100 µg/ml of Ampicillin and grown overnight with shaking at 37° C. After overnight growth, separate 1 L cultures of LB supplemented with 100 µg/ml of Ampicillin were inoculated with 5 ml of the individual cultures and incubated at 37° C. with shaking until reaching an optical density of 0.4 OD per ml at a wavelength of 595 nm. At an optical density of 0.4 OD per milliliter, these cultures were induced for protein overexpression by addition of Isopropyl β-D-1 thiogalactopyranoside (IPTG) at a final concentration of 1 mM. The cells were grown for 2 hours at 37° C. post-induction followed by harvesting via centrifugation. Harvested bacterial cell pellets were flash frozen in liquid nitrogen and stored at −80° C.

PARP proteins: Uninfected Serum Free Sf9 cells, cultured in SF-II 900 media (Invitrogen) were plated onto 10 cm diameter cell culture plates at a density of $1 \times 10^6$ cells per milliliter of culture. The cells were transfected with 1 µg of bacmid for expression of PARP1 or PARP3 using Cellfectin transfection reagent, as described by manufacturer (Invitrogen). After 5 hours, filter sterilized FBS, Penicillin, and Streptomycin were added to final concentrations of 10%, 100 I.U. per milliliter, and 100 µg/ml, respectively. After three days, the cell culture medium was collected, which contained the desired baculovirus. Following two subsequent rounds of infection and amplification, a 150 ml culture of Sf9 cells in SF-II 900 media with 10% FBS in a sterile spinner flask was infected for overexpression of either PARP1 or PARP3. Two days after infection, the Sf9 cells expressing either PARP1 or PARP3 were collected by centrifugation, washed once with cold PBS, pelleted in a 50 mL plastic tube, flash frozen with liquid $N_2$, and stored at −80° C. for future use.

Protein Purification:

The recombinant ARBD-Fc fusions, PARP1, and PARP3 were expressed as described below.

ARBD-Fc Fusion Proteins: Induced frozen bacterial cell pellets were thawed on wet ice until liquid and lysed by sonication in IMAC Lysis Buffer (10 mM Tris pH 7.5, 0.5 M NaCl, 0.1 mM EDTA, 0.1% NP-40, 10% Glycerol, 10 mM Imidazole, 1 mM PMSF, 1 mM β-Mercaptoethanol). The lysate was clarified by high speed centrifugation at 15,000 RPM for 30 minutes at 4° C. in an SS34 Rotor. The clarified supernatant was applied to 1 mL bed volume of Ni-NTA Resin (QIAGEN) equilibrated in IMAC Equilibration Buffer (10 mM Tris pH 7.5, 0.5 M NaCl, 0.1% NP-40, 10% Glycerol, 10 mM Imidazole) and incubated at 4° C. for 2 hours on a Nutator. IMAC beads were washed 4 times in 30 mL of IMAC Wash Buffer (10 mM Tris 7.5, 1 M NaCl, 0.2% NP-40, 10% Glycerol, 10 mM Imidazole, 1 mM PMSF) with collection by centrifugation. The purified ARBD-Fc fusion proteins were eluted by three consecutive washes of IMAC elution buffer (10 mM Tris pH 7.5, 0.2 M NaCl, 0.1% NP-40, 10% Glycerol, 500 mM Imidazole, 1 mM PMSF, 1 mM β-Mercaptoethanol). Eluates were combined and dialyzed overnight in IMAC Dialysis Buffer (10 mM Tris pH 7.5, 0.2 M NaCl, 10% Glycerol, 1 mM PMSF, 1 mM β-Mercaptoethanol). Dialysate containing the purified fusion proteins was collected, spun at maximum speed in a microcentrifuge to remove any debris, and quantified using a Bradford Protein Assay. The fusion proteins were aliquoted in 100 µg amounts for future use, flash frozen with liquid $N_2$, and stored at −80 degrees Celsius.

PARP1 and PARP3: PARP1- or PARP3-expressed frozen Sf9 cell pellets from 150 mL of cell culture were thawed on wet ice. The cells were resuspended in 7 ml of FLAG PARP Lysis Buffer [20 mM HEPES pH 7.9, 0.5 M NaCl, 4 mM $MgCl_2$, 0.4 mM EDTA, 20% Glycerol, 250 mM Nicotinamide, 2 mM β-Mercaptoethanol, 2× Protease Inhibitor cocktail (Roche)] and dounced 10 times on ice with tight pestle in a Wheaton dounce homogenizer. The lysate was centrifuged for 30 min. at 15,000 RPM at 4° C. in an SS34 Rotor. The clarified supernatant was removed, mixed with an equal volume of FLAG Dilution Buffer (20 mM HEPES pH 7.9, 10% Glycerol, 0.02% NP-40), and sonicated with a Branson Digital Sonifier for 15 seconds at 65% amplitude in a salt ice bath. The lysate was centrifuged again as described above and the clarified lysate was removed. Clarified lysate was applied to 200 µl of FLAG resin equilibrated in FLAG PARP Wash Buffer #1 (20 mM HEPES pH 7.9, 150 mM NaCl, 2 mM $MgCl_2$, 0.2 mM EDTA, 15% Glycerol, 0.01% NP-40, 100 mM Nicotinamide, 0.2 mM β-Mercaptoethanol, 1 mM PMSF, 1 µM Aprotinin, 100 µM Leupeptin) and incubated at 4° C. for 3 hours on a Nutator. The resin was washed once with 100 volumes of FLAG PARP Wash Buffer #1, twice with FLAG PARP Wash Buffer #2 (20 mM HEPES pH 7.9, 1 M NaCl, 2 mM $MgCl_2$, 0.2 mM EDTA, 15% Glycerol, 0.01% NP-40, 100 mM Nicotinamide, 0.2 mM β-Mercaptoethanol, 1 mM PMSF, 1 µM Aprotinin, 100 µM Leupeptin), and twice with FLAG PARP Wash Buffer #3 (20 mM HEPES pH 7.9, 150 mM NaCl, 2 mM $MgCl_2$, 0.2 mM EDTA, 15% Glycerol, 0.01% NP-40, 0.2 mM β-Mercaptoethanol, 1 mM PMSF). Purified PARP1 and PARP3 were eluted from the resin using FLAG PARP Wash Buffer #3 containing 0.2 mg/mL FLAG peptide. Eluted proteins were distributed in 10 µl aliquots, flash frozen with liquid $N_2$, and stored at −80° C. until use.

In Vitro PARylation of Model Substrates:

PARP1 and PARP3 were incubated with either reaction buffer alone (20 mM HEPES, 5 mM $MgCl_2$, 5 mM $CaCl_2$, 0.01% NP-40, 25 mM KCl, 1 mM DTT, 0.1 mg/mL BSA, 0.1 mg/mL sssDNA), as a negative control or with $NAD^+$. Mono(ADP-ribose) was generated by incubation of 2 µM PARP3 with 250 µM $NAD^+$ for 30 minutes at room temperature. Oligo(ADP-ribose) was generated by incubation of 1 µM PARP1 with 3 µM NAD+ for 30 minutes at room temperature. Poly(ADP-ribose) was generated by incubation of 100 nM PARP1 with 250 µM $NAD^+$ for 5 minutes. Reactions were stopped by addition of on third reaction volume 4×SDS Loading Buffer (8% SDS, 0.4% Bromophenol Blue, 20% Glycerol, 700 mM β-Mercaptoethanol).

ADP-Ribose Detection Using ARBD-Fc Fusion Proteins:

Two hundred and fifty ng of PARP3 with mono(ADP-ribose), 85 ng of PARP1 with oligo(ADP-ribose), or 8.5 ng of PARP1 with poly(ADP-ribose) or three-fold serial dilutions of each were spotted onto dry nitrocellulose membrane (dot blots). Alternatively these samples (in quantities as noted above, or similar quantities of unmodified PARP1 or PARP3 controls) were resolved by 10% PAGE-SDS and transferred to a nitrocellulose membrane (Western blots). Both the dot blots and Western blots were incubated for 1 hour at room temperature in 5% (w/v) non-fat milk in TBST (Tris buffered saline with Tween-20) with shaking. The blots were washed thoroughly with TBST and then incubated with a specific ARBD-Fc fusion protein at 10 ng/µl in 1% (w/v) non-fat milk in TBST for 1 hour at room temperature with shaking. Membranes were again washed thoroughly with TBST and incubated for 1 hour with 1:8000 dilution Goat anti-Rabbit antibody conjugated to horse radish peroxidase (Thermo) in 1% (w/v) non-fat milk powder in TBST for 1 hour at room temperature with shaking. The membranes were washed thoroughly with TBST, developed with Super-Signal West Chemiluminescent reagents (Pierce), and detected with a Chemi-Doc system (Bio-Rad).

Example 2

Results

The inventors describe the production and application of antibody-like ADP-ribose binding proteins comprising one of a number of different ADP-ribose binding domains (ARBDs) fused the Fc region of an immunolglobulin (FIGS. 1.1-1.5). The recombinant fusion proteins can be purification in large (i.e., milligram) quantities of nearly homogenous and well-characterized protein from plasmid vectors (FIGS. 2 and 3).

Figure 4:
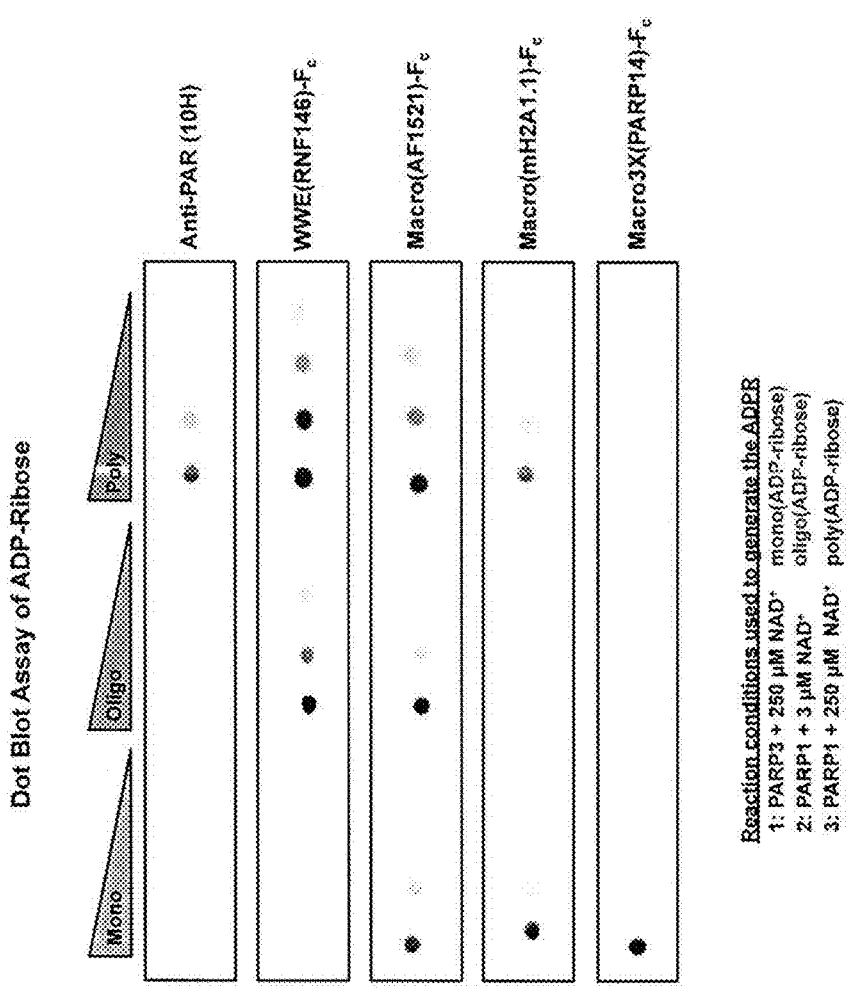
FIG. 4. Dot blot assays of mono, oligo, and poly-ADP-ribose binding by ADP-ribose binding domain-Fc fusion proteins. Mono-ADP-ribose was generated by incubating purified recombinant mouse PARP3 with $NAD^+$ in the presence of DNA, resulting in auto-mono-ADP-ribosylated PARP3 protein. Oligo and poly-ADP-ribose was generated by incubating purified recombinant mouse PARP1 with NAD+ (modulating the amount of PARP1, concentration of NAD+, and length of time to control the length of polymer production) in the presence of DNA, resulting in auto-oligo-ADP-ribosylated (less than 10 ADP-ribose units) or auto-poly-ADP-ribosylated PARP1 protein. The ADP-ribosylated proteins were spotted onto a nitrocellulose membrane in decreasing amounts as shown, then blotted using the indicated ARBD-Fc fusion proteins with a goat anti-rabbit IgG HRP detection system.
Figure 5:
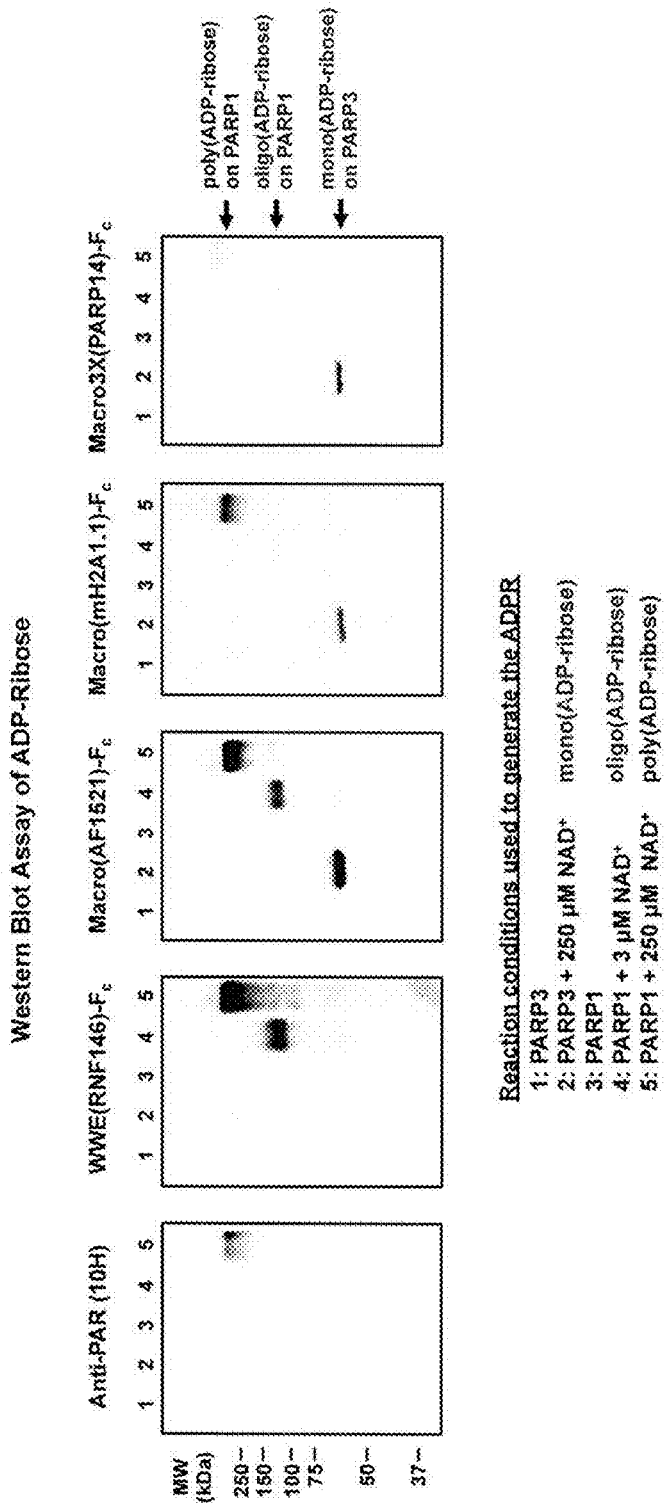
FIG. 5. Western blot assays of mono, oligo, and poly-ADP-ribose binding by ADP-ribose binding domain-Fc fusion proteins. Mono-ADP-ribose on PARP3, and oligo-ADP-ribose and poly-ADP-ribose PARP1 were generated as described in FIG. 3. The ADP-ribosylated proteins, as well as non-ADP-ribosylated versions of PARP1 and PARP3 (as controls) were run on a 10% PAGE-SDS resolving gel and transferred onto a nitrocellulose membrane, then blotted using the indicated ARBD-Fc fusion proteins with a goat anti-rabbit IgG HRP detection system. The locations of the mono-ADP-ribosylated PARP3, oligo-ADP-ribosylated PARP1, and poly-ADP-ribosylated PARP1 bands are indicated by the labeled arrows. The molecular weights (MW) in kilodaltons (kDa) of marker proteins run on the same gels are shown.

The ADP-ribose binding domains chosen to exemplify the utility of this disclosure are the *H. sapiens* WWE domain from protein RNF146 (FIG. 1.1), the *A. fulgidus* AF1521 macro domain (FIG. 1.2), the *H. sapiens* macrodomain from histone variant macroH2A1.1 (FIG. 1.3), the *H. sapiens* macrodomain triplet from PARP14 (FIG. 1.4). The WWE domain was chosen as an ADP-ribose binding domain due to its unique mode of binding to poly(ADP-ribose). The WWE domain from the RNF146 protein binds to the connection between ADP-ribose moieties in oligo and poly(ADP-ribose) chains, allowing its use as a oligo and poly(ADP-ribose) specific reagent (FIGS. 4 and 5). The AF1521 macrodomain was chosen as a general ADP-ribose binding module (FIGS. 4 and 5), since it has the highest reported affinity to ADP-ribose of any form for any macrodomain yet reported. Similarly, the macroH2A1.1 macrodomain was chosen for its ability to bind mono- and poly-ADP-ribose (FIGS. 4 and 5). The PARP14 triple macrodomain was chosen due to its reported preference for mono(ADP-ribose) as a target (FIGS. 4 and 5).

The sequence content of ADP-ribose binding domains and the Fc portion of immunoglobulin were guided by and largely limited to reported functional crystallizable fragments of chosen domains or the homology to reported crystallizable fragments. The construct encodes for a protein with an N-terminal decahistidine tag ($His_{10}$), an optional Strep (II) tag, the ADP-ribose binding domain, a flexible glycine and serine rich linker, and the Fc region of an immunoglobulin (FIGS. 1.1-1.5). The basic outline of the ARBD-Fc fusions were designed such that they contain a modular construction, wherein any ARBD could be easily placed into the construct by way of traditional cloning methods using the convenient NdeI and SalI sites flanking the ADP-ribose binding domain, which is responsible for substrate specificity (FIG. 2). These ADP-ribose binding domains were cloned into the pET19b *E. coli* expression system, (FIG. 2) where the constructs expressed well yielding many milligrams of soluble purifiable protein per liter of culture (FIG. 3). Any relate vector with similar features could be used as well.

In order to test the specificity and affinity of these ARBD-Fc fusion constructs, they were purified and screened against prepared model substrates of mono-ADP-ribose, a short version of the polymer called oligo-ADP-ribose (<10 ADP-ribose units), and a lengthy version of the polymer called poly-ADP-ribose (FIG. 3). Using both dot blotting and Western blotting approaches, the commercially available 10H antibody along with the different ARBD-Fc fusion proteins show distinctly different patterns of recognition, demonstrably related to their known biophysical modes of recognition of ADP-ribosylation. As reported in the literature, the 10H antibody binds to extensive poly(ADP-ribosyl)ation (>~10 ADP-ribose units), but does not bind to mono- or oligo-ADP-ribose (FIGS. 4 and 5). The WWE domain-containing fusion construct, which should bind to 2 or more units of poly(ADP-ribose) since it biochemically identifies junctions between ADP-ribose units, binds both oligo and poly(ADP-ribose) with great specificity and affinity (FIGS. 3 and 4). The AF1521 macro domain-containing fusion binds well to all prepared substrates with a high affinity, likely owed to its nanomolar affinity for ADP-ribose (FIGS. 3 and 4). The macroH2A1.1 macro domain fusion protein binds to both mono- and poly-ADP-ribose (FIGS. 3 and 4). The PARP14 triple macro domain fusion protein binds preferentially to mono-ADP-ribose, as has been reported previously (FIGS. 3 and 4).

Figure 6:
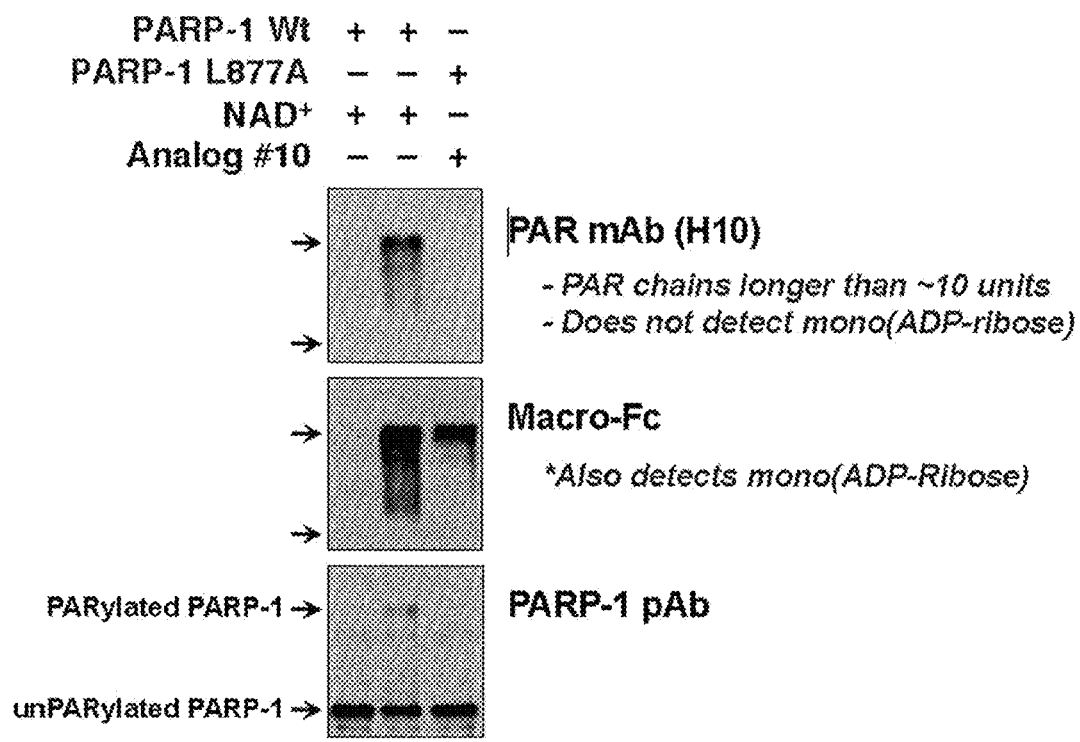
FIG. 6. Macro(AF1521)-$F_c$ detects an ADP-ribose analog generated from NAD+ modified at the 8-position of the adenine ring. ADP-ribosylated PARP-1 and 8-analog-ADP-ribosylated PARP-1 were generated by incubating purified recombinant wild-type human PARP-1 or an analog-sensitive human PARP-1 mutant (L877A) with NAD+ or 8-analog-NAD+, respectively, in the presence of DNA, resulting in auto-poly-ADP-ribosylated PARP1 proteins. The ADP-ribosylated proteins were run on a 10% PAGE-SDS resolving gel and transferred onto a nitrocellulose membrane, then blotted using PAR mAb 10H (top) or Macro(AF1521)-$F_c$ fusion protein (middle), or PARP-1 pAb (bottom) with an anti-IgG HRP detection system. The molecular weights (MW) in kilodaltons (kDa) of marker proteins run on the same gels are shown.

The use of modified analogs of NAD+, for example versions modified at position 8 of the adenine ring, has proven to be an effective approach for studying the functions of PARPs. One issue with this approach, however, is that the 10H monoclonal antibody cannot bind to and, hence, does not detect 8-analog-PAR, as shown in FIG. 6. In contract, ADPR detection reagents, such as Macro(AF1521)-$F_c$, detects 8-analog-PAR (FIG. 6).

Figure 7:
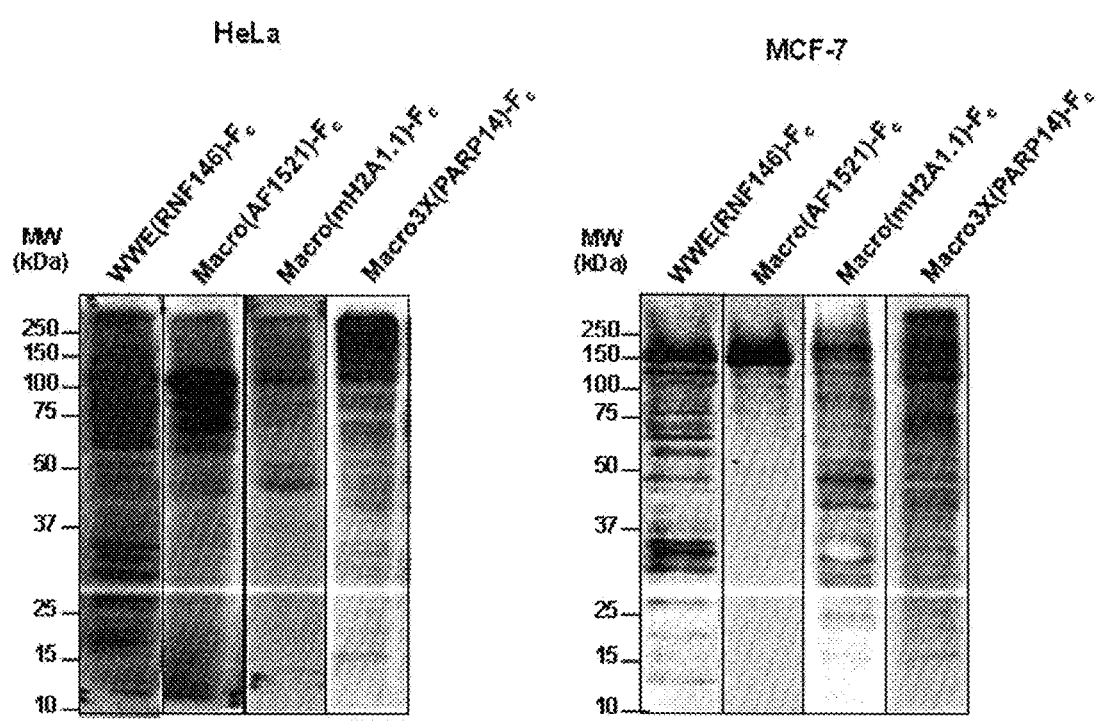
FIG. 7. Western blot assays of mono, oligo, and poly-ADP-ribose binding by ADP-ribose binding domain-Fc fusion proteins in nuclear extracts from cancer cell lines. Nuclear extracts were prepared from cervical cancer cells (HeLa) and breast cancer cells (MCF-7). The extracts were run on a 10% PAGE-SDS resolving gel and transferred onto a nitrocellulose membrane, then blotted using the indicated ARBD-Fc fusion proteins with a goat anti-rabbit IgG HRP detection system. The molecular weights (MW) in kilodaltons (kDa) of marker proteins run on the same gels are shown.
Figure 8:
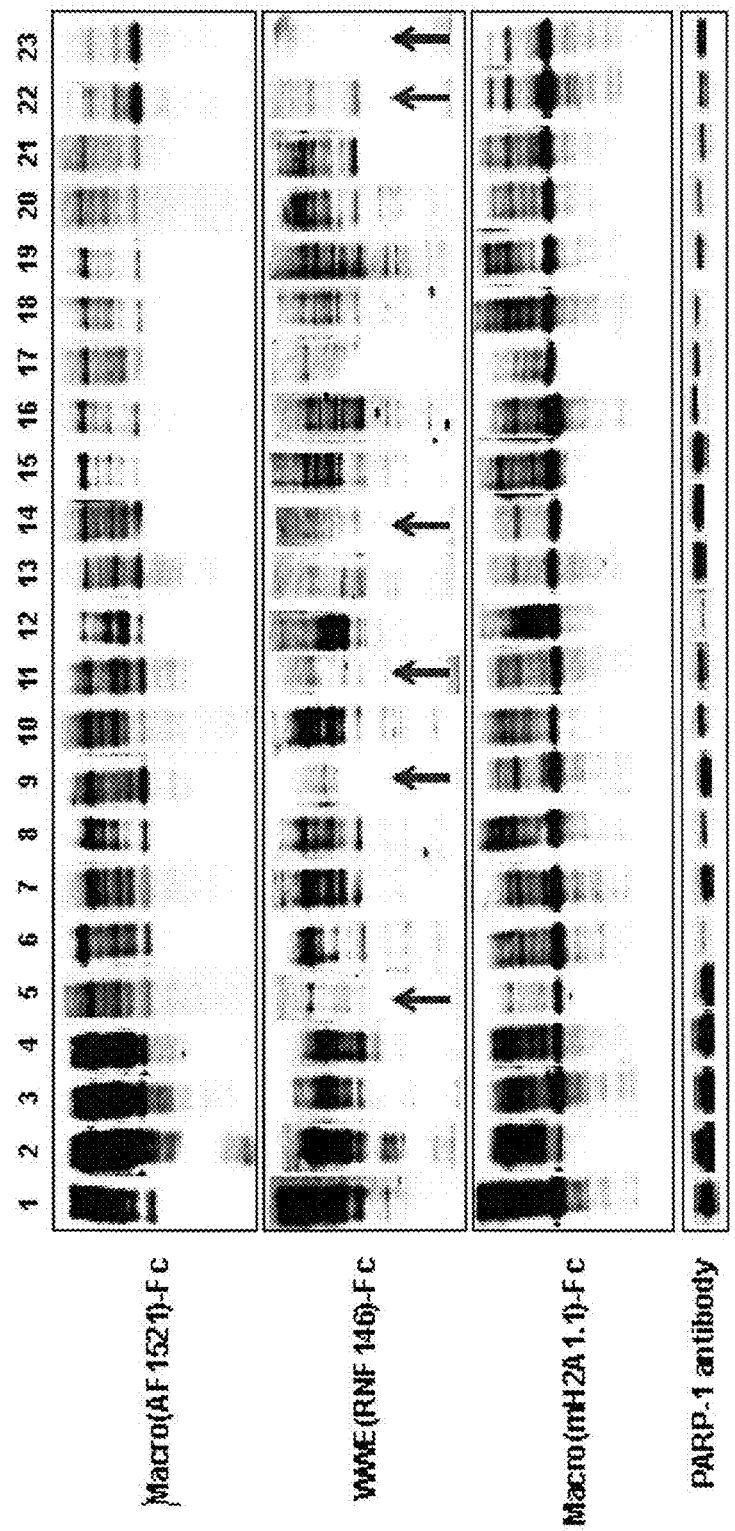
FIG. 8. Western blot assays of mono, oligo, and poly-ADP-ribose in ovarian cancer cells as detected by ADP-ribose binding domain-Fc fusion proteins. Nuclear extracts were prepared from ovarian cancer biopsies. The extracts were run on a 10% PAGE-SDS resolving gel and transferred onto a nitrocellulose membrane, then blotted using the indicated ARBD-Fc fusion proteins, as well as an antibody against PARP-1, with a goat anti-rabbit IgG HRP detection system. Arrows indicate samples that exhibit the greatest difference in the ratios between the signals for Macro (AF1521)-Fc and WWE(RNF146)-Fc.

Many PARPs such as the nuclear PARPs (PARPs 1, 2, and 3), are emerging as potential targets for cancer therapies. Thus, the ability to detect the products of the enzymatic activities, e.g., mono-, oligo-, and polyADPR, is cancers can be very important clinically and may have important diagnostic implications. In this regard, the ADP-ribose binding domain-Fc fusion proteins detect all forms of ADP in nuclear extracts from the HeLa cancer cells (FIG. 7) and ovarian cancer biopsies (FIG. 8). Furthermore, results from the ovarian cancer biopsies show differences in the ratios between the different ADPR detection reagents. For example, samples 5, 9, 11, 14, 22, and 23 showed robust signals with Macro(AF1521)-Fc, but relatively weak signals with WWE(RNF146)-Fc (FIG. 8). These differences are likely to be indicative of the clinical status of the cancers.

Example 3

Discussion

Here, the inventors describe the design, creation, and use of a novel and superiorly sensitive approach to detect ADP-ribosylation modifications. Where before, detection of ADP-ribosylation was only possible on extensively post-translationally modified proteins using a monoclonal antibody, the inventors have now generated a series of protein fusions capable of detecting mono, oligo, and poly(ADP-ribosyl)ated substrates with great sensitivity and specificity. These immune-based ADP-ribose detection reagents use a modular design, whereby one or more ADP-ribose-binding domains are fused to the Fc region of an immunoglobulin, which facilitates their use in the all biotechnological applications currently designed for antibodies. This spectrum of reagents allows more sensitive detection of all forms of the ADP-ribose modification than previously possible with available reagents. Moreover these reagents can detect mono (ADP-ribose), and oligo(ADP-ribose), where no reagent capable of this feat existed before.

This collection of fusion proteins allows detection of multiple different forms of ADP-ribose (mono, oligo, poly) with affinities and specificities that are not observed with available reagents (e.g., the 10H monoclonal antibody) with the functionality of an immune-related reagent. An advantage of this approach is that the domains conferring ADP-ribose specificity use well characterized biophysical mechanisms for mono, oligo, or poly-ADP-ribose recognition, allowing predictably identification of the target modifications. In this way the reagent can be made to act in a predictable and rational manner related to the domain of choice, whereas an antibody, such as the 10H anti-PAR monoclonal antibody, binds its target in an uncharacterized and biophysically unknown manner. In addition, the recombinant nature of the fusion proteins allows purification of large quantities of nearly homogenous and well-characterized protein from plasmid vectors (FIGS. 2 and 3).

Current understanding of cellular ADP-ribosylation is that its use as a post-translational modification is often in the context of rapid signal transduction, often being a marker of various types of cellular stress. Where previously only the most egregious DNA lesion-induced PARylation events were routinely detectable using current technology, the sensitive and substrate-specific reagents described herein constitute a new method for understanding how ADP-ribosylation might play a role in more subtly important biological events. Even more importantly, the combination of these reagents on a given set of biological samples now allows parsing of the type of modification contributing to, or correlated with, a particular biological process, including disease states such as cancer. By using the ARBD-Fc Fusion proteins which can detect either all ADP-ribosylated substrates, mono(ADP-ribosyl)ated substrates, or oligo and poly(ADP-ribasyl)ated substrates, the type of ADP-ribosylation content of a biological sample can be deduced using these reagents. This type of specificity, heretofore unachievable using current technology, may also be used to shed light on clinical trials using PARP protein inhibitors in order to screen patient samples and determine whether their ADP-ribosylation content reflects study outcomes.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. References

The following references, to the extent that they provide exemplary procedural or other details supplementary to those set forth herein, are specifically incorporated herein by reference:

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,683,202
U.S. Pat. No. 4,684,611
U.S. Pat. No. 4,714,682
U.S. Pat. No. 4,767,206
U.S. Pat. No. 4,774,189
U.S. Pat. No. 4,857,451
U.S. Pat. No. 4,879,236
U.S. Pat. No. 4,938,948
U.S. Pat. No. 4,952,500
U.S. Pat. No. 4,989,977
U.S. Pat. No. 5,021,236
U.S. Pat. No. 5,160,974
U.S. Pat. No. 5,196,066
U.S. Pat. No. 5,217,879
U.S. Pat. No. 5,302,523
U.S. Pat. No. 5,322,783
U.S. Pat. No. 5,384,253
U.S. Pat. No. 5,440,013
U.S. Pat. No. 5,446,128
U.S. Pat. No. 5,464,765
U.S. Pat. No. 5,475,085
U.S. Pat. No. 5,478,722
U.S. Pat. No. 5,506,138
U.S. Pat. No. 5,538,877
U.S. Pat. No. 5,538,880
U.S. Pat. No. 5,550,318

U.S. Pat. No. 5,563,055
U.S. Pat. No. 5,580,859
U.S. Pat. No. 5,589,466
U.S. Pat. No. 5,610,042
U.S. Pat. No. 5,618,914
U.S. Pat. No. 5,656,610
U.S. Pat. No. 5,670,155
U.S. Pat. No. 5,670,488
U.S. Pat. No. 5,672,681
U.S. Pat. No. 5,674,976
U.S. Pat. No. 5,702,932
U.S. Pat. No. 5,710,245
U.S. Pat. No. 5,736,524
U.S. Pat. No. 5,780,448
U.S. Pat. No. 5,789,215
U.S. Pat. No. 5,824,544
U.S. Pat. No. 5,830,725
U.S. Pat. No. 5,840,833
U.S. Pat. No. 5,849,304
U.S. Pat. No. 5,851,826
U.S. Pat. No. 5,858,744
U.S. Pat. No. 5,859,184
U.S. Pat. No. 5,871,983
U.S. Pat. No. 5,871,986
U.S. Pat. No. 5,879,934
U.S. Pat. No. 5,888,502
U.S. Pat. No. 5,889,155
U.S. Pat. No. 5,925,565
U.S. Pat. No. 5,928,906
U.S. Pat. No. 5,929,237
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
U.S. Pat. No. 6,093,573
U.S. Pat. No. 6,261,569
U.S. Patent Appln. 2005/0015232
Ahel et al., *Nature.* 451(7174):81-5, 2008.
Armentano et al., *Proc. Natl. Acad. Sci. USA*, 87(16):6141-6145, 1990.
Bett et al., *J. Virology*, 67(10):5911-5921, 1993.
Bilbao et al., *FASEB J.*, 11(8):624-634, 1997.
Blomer et al., *J. Virol.*, 71(9):6641-6649, 1997.
Bodanszky et al., *J. Antibiol.*, 29(5):549-53, 1976.
Buelow et al., *J Biol Chem.* 283(36):24571-83, 2008.
Capaldi et al., *Biochem. Biophys. Res. Comm.*, 74(2):425-433, 1977.
Caplen et al., *Gene Ther.*, 6(3):454-459, 1999.
Carbonelli et al., *FEMS Microbiol. Lett.*, 177(1):75-82, 1999.
Chandler et al., *Proc. Natl. Acad. Sci. USA*, 94(8):3596-601, 1997.
Chen and Okayama, *Mol. Cell Biol.*, 7(8):2745-2752, 1987.
Chillon et al., *J. Virol.*, 73(3):2537-2540, 1999.
Cocea, *Biotechniques*, 23(5):814-816, 1997.
Coffey et al., *Science*, 282(5392):1332-1334, 1998.
Cohen et al., *J. Med. Chem.*, 33:883-894, 1990.
DeLuca et al., *J. Virol.*, 56(2):558-570, 1985.
Derby et al., *Hear Res*, 134(1-2):1-8, 1999.
Egloff et al., *J. Virol.* 80(17):8493-502, 2006.
Fahrer et al., *Nucleic Acids Res.* 35(21):e143, 2007.
Fechheimer et al., *Proc Natl. Acad. Sci. USA*, 84:8463-8467, 1987.
Feng et al., *Nat. Biotechnol.*, 15(9):866-870, 1997.
Garoff and Li, *Curr. Opin. Biotechnol.*, 9(5):464-469, 1998.
Garrido et al., *J. Neurovirol.*, 5(3):280-288, 1999.
Gnant et al., *Cancer Res.*, 59(14):3396-403, 1999a.
Gnant et al., *J. Natl. Cancer Inst.*, 91(20):1744-1750, 1999b.
Gopal, *Mol. Cell Biol.*, 5:1188-1190, 1985.
Graham and Prevec, *Mol Biotechnol*, 3(3):207-220, 1995.
Graham and Van Der Eb, *Virology*, 52:456-467, 1973.
Gronenborn et al., *Anal. Chem.*, 62(1):2-15, 1990.
Haecker et al., *Hum. Gene Ther.*, 7(15):1907-1914, 1996.
Harland and Weintraub, *J. Cell Biol.*, 101(3):1094-1099, 1985.
Hayashi et al., *Neurosci. Lett.*, 267(1):37-40, 1999.
Holzer et al. *Virology*, 253(1):107-114, 1999.
Howard et al., *Ann. NY Acad. Sci.*, 880:352-365, 1999.
Imai et al., *Nephrologie*, 19(7):397-402, 1998.
Jackson, *Seminars in Oncology*, 24:L164-172, 1997.
Jones et al., *Br. J. Pharmacol.*, 145(8):1093-102, 2005.
Kaeppler et al., *Plant Cell Rep.*, 8:415-418, 1990.
Kaneda et al., *Science*, 243:375-378, 1989.
Karras et al., *EMBO J.* 24(11):1911-20, 2005.
Kato et al, *J. Biol. Chem.*, 266:3361-3364, 1991.
Kaufman et al., *Arch. Ophthalmol.*, 117(7):925-928, 1999.
Kohut et al., *Am. J. Physiol.*, 275(6Pt1):L1089-1094, 1998.
Kooby et al., *FASEB J*, 13(11):1325-34, 1999.
Krisky et al., *Gene Ther*, 5(11):1517-1530, 1998a.
Krisky et al., *Gene Ther*, 5(12):1593-1603, 1998b.
Lachmann and Efstathiou, *Curr. Opin. Mol. Ther.*, 1(5):622-632, 1999.
Levenson et al., *Hum. Gene Ther.*, 9(8):1233-1236, 1998.
Lundstrom, *J. Recept Signal Transduct. Res.*, 19(1-4):673-686, 1999.
Macejak and Sarnow, *Nature*, 353:90-94, 1991.
Marienfeld et al., *Gene Ther.*, 6(6):1101-1113, 1999.
Mastrangelo et al., *Biotechnol. Bioeng.*, 65(3):298-305, 1999.
Merrifield, *J. Am. Chem. Soc.*, 85:2149-2154, 1963.
Miyatake et al., *Gene Ther.*, 6:564-572, 1999.
Moriuchi et al., *Cancer Res*, 58(24):5731-5737, 1998.
Morrison et al., *J. Gen. Virol.*, 78(Pt 4):873-878, 1997.
Naldini et al., *Science*, 272(5259):263-267, 1996.
Navia et al., *Curr. Opin. Struct. Biol.*, 2:202-210, 1992.
Neumann et al., *Proc. Natl. Acad. Sci. USA*, 96(16):9345-9350, 1999.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
Parks et al., *J. Virol.*, 71(4):3293-8, 1997.
PCT Appln. PCT/US00/14667
PCT Appln. PCT/US99/11913
PCT Appln. PCT/US99/18441
PCT Appln. WO 94/09699
Pelletier and Sonenberg, *Nature*, 334(6180):320-325, 1988.
Peptide Synthesis, 1985.
Petermann et al., *DNA Repair (Amst).* 2(10):1101-14, 2003.
Pleschke et al., *Biol Chem.* 29; 275(52):40974-80, 2000.
Potrykus et al., *Mol. Gen. Genet.*, 199(2):169-177, 1985.
Protective Groups in Organic Chemistry, 1973
Protein NMR Spectroscopy, Principles and Practice, Cavanagh et al., Academic Press, San Diego, 1996.
Reddy et al., *Virology*, 251(2):414-26, 1998.
Rippe, et al., *Mol. Cell Biol.*, 10:689-695, 1990.
Robbins and Ghivizzani, *Pharmacol Ther*, 80(1):35-47, 1998.
Robbins et al., *Trends Biotechnol.*, 16(1):35-40, 1998.

Sambrook et al., In: *Molecular cloning: a laboratory manual*, 2nd Ed., Cold Spring Harbor Laboratory Press, Cold Spring Harbor, N.Y., 1989.
Sawai et al., *Mol. Genet. Metab.,* 67(1):36-42, 1999.
Solid Phase Peptide Synthelia, 1984
Suzuki et al., *Biochem Biophys Res Commun*, 252(3):686-90, 1998.
Timiryasova et al., *Int. J. Oncol.,* 14(5):845-854, 1999.
Walker et al., *Biochem Biophys Res Commun.* 342(1):336-41, 2006.
Wang et al., *Infect. Immun.,* 66:4193-202, 1998.
Wider, *BioTechniques,* 29:1278-1294, 2000.
Wilson, *J. Clin. Invest.,* 98(11):2435, 1996.
Wong et al., *Gene,* 10:87-94, 1980.
Yamada et al., *Brain Res.,* 833(2):302-307, 1999.
Yeung et al., *Gene Ther.,* 6(9):1536-1544, 1999.
Yoon et al., *J. Gastrointest. Surg.,* 3(1):34-48, 1999.
Zheng et al., *J. Gen. Virol.,* 80(Pt 7):1735-1742, 1999.
Zufferey et al., *Nat. Biotechnol.,* 15(9):871-875, 1997.

---

What is claimed is:

1. A fusion protein comprising (a) an Fc domain and (b) a first ADP-ribose binding domain.

2. The fusion protein of claim 1, wherein said Fc domain is located N-terminal to said first ADP-ribose binding domain.

3. The fusion protein of claim 1, wherein said Fc domain is located C-terminal to said first ADP-ribose binding domain.

4. The fusion protein of claim 1, wherein said Fc domain is a non-human Fc domain.

5. The fusion protein of claim 1, wherein said Fc domain is a human Fc domain.

6. The fusion protein of claim 5, wherein said human Fc domain is an IgG, IgA, IgM, IgE or IgD Fc domain.

7. The fusion protein of claim 1, wherein said first ADP-ribose binding domain is a mammalian WWE ADP-ribose binding domain, an archeon *A. fulgidus* macrodomain ADP-ribose binding domain or a mammalian MACROD1 or MACROD2 ADP-ribose binding domain.

8. The fusion protein of claim 1, further comprising hinge region.

9. The fusion protein of claim 1, further comprising a label or purification tag.

10. The fusion protein of claim 1, further comprising a linker disposed between said Fc domain and said first ADP-ribose domain.

11. The fusion protein of claim 1, further comprising a second ADP-ribose binding domain.

12. The fusion protein of claim 1, wherein said Fc domain does not comprise antigen binding domains and said first ADP-ribose binding domain is linked to other polypeptide sequences naturally associated with said ADP-ribose binding domain.

13. The fusion protein of claim 1, consisting essentially of said Fc domain, said first ADP-ribose binding domain, a His(10) tag, a Strep(II) tag, and a linker disposed between said Fc domain and said first ADP-ribose binding domain.

14. An expression vector comprising a nucleic acid segment encoding the fusion protein according to claim 1, wherein said nucleic acid segment is under the operational control of a promoter.

15. The expression vector of claim 14, wherein said promoter is a bacterial promoter or a eukaryotic promoter.

16. The expression vector of claim 14, further comprising a multiple cloning site positioned adjacent to an Fc domain coding sequence, and/or further comprising a bacterial origin of replication, and/or a selectable marker.

17. The expression vector of claim 15, wherein said expression vector comprises a LacI gene and an AmpR gene.

18. A method of detecting an ADP-ribose-containing molecule comprising contacting a sample suspected or known to contain a first ADP-ribose-containing molecule with a first fusion protein according to claim 1.

19. The method of claim 18, wherein said first ADP-ribose-containing molecule comprises an ADP-ribose monomer, an ADP-ribose oligomer or an ADP-ribose polymer.

20. The method of claim 18, wherein said method further comprises contacting said sample with an anti-ADP ribose antibody distinct from said first fusion protein.

21. The method of claim 18, further comprising contacting said sample with a second fusion protein that has a different ADP-ribose-binding specificity as compared to said first fusion protein, and said first and second fusion proteins are differentially detectable.

22. The method of claim 21, wherein said first fusion protein detects ADP-ribose monomers and said second fusion protein detects ADP-ribose oligomers or ADP-ribose polymers.

23. The method of claim 21, wherein said first fusion protein detects ADP-ribose oligomers and said second fusion protein detects ADP-ribose polymers.

24. The method of claim 18, wherein said fusion proteins are detected via Western blot, ELISA, RIA, immunoprecipitation, immunofluorescent cell staining, FACS or chromatin immunoprecipitation.

25. A method of determining ADP-ribose monomer, oligomer and polymer levels in a cancer cell from a sample comprising:
   (a) contacting a cancer cell from said sample with a first fusion protein comprising comprising (i) an Fc domain and (ii) at least one ADP-ribose binding domain, wherein said first fusion protein recognizes ADP-ribose monomers;
   (b) contacting said cancer cell with a second fusion protein comprising (i) an Fc domain and (ii) at least one ADP-ribose binding domain, wherein said second fusion protein recognizes ADP-ribose oligomers;
   (c) contacting said cancer cell with an antibody that recognizes ADP-ribose polymers larger than oligomers;
   (d) measuring the binding of said first and second fusion proteins and said antibody to said cell, and
   (e) comparing binding patterns, wherein binding only of said first fusion protein indicates the presence of monomers, binding of both said first and second fusion proteins indicates the presence of oligomers, and binding of said first and second fusion proteins and said antibody indicates the presence of polymers.

26. The method of claim 25, wherein said Fc domain of said first and/or second fusion protein is located N-terminal to said ADP-ribose binding domain.

27. The method of claim 25, wherein said Fc domain of said first and/or second fusion protein is located C-terminal to said ADP-ribose binding domain.

28. The method of claim 25, wherein said Fc domain of said first and/or second fusion protein is a non-human Fc domain.

29. The method of claim 25, wherein said Fc domain of said first and/or second fusion protein is a human Fc domain.

30. The method of claim 29, wherein said human Fc domain of said first and/or second fusion protein is an IgG, IgA, IgM, IgE or IgD Fc domain.

31. The method of claim 25, wherein said ADP-ribose binding domain of said first and/or second fusion protein is a mammalian WWE ADP-ribose binding domain, an archeon *A. fulgidus* macrodomain ADP-ribose binding domain or a mammalian MACROD1 or MACROD2 ADP-ribose binding domain.

32. The method of claim 25, wherein said first and/or second fusion protein further comprises hinge region.

33. The method of claim 25, wherein said first and/or second fusion protein further comprising a label or purification tag.

34. The method of claim 33, wherein the purification tag is a poly-His tag, a Strep(II) tag, or an epitope tag.

35. The method of claim 25, wherein said first and/or second fusion proteins further comprise a linker disposed between said Fc domain and said ADP-ribose domain.

36. The method of claim 25, wherein said Fc domain of said first and/or second fusion protein does not comprise antigen binding domains and said ADP-ribose binding domain is isolated away from polypeptide sequences naturally associated with said ADP-ribose binding domain.

37. The method of claim 25, wherein said first and/or second fusion protein consists essentially of said Fc domain, said ADP-ribose binding domain, a His(10) tag, a Strep(II) tag, and a linker disposed between said Fc domain and said ADP-ribose binding domain.

38. The method of claim 25, wherein said cancer cell is a breast cancer cell, a brain cancer cell, a lung cancer cell, a liver cancer cell, a prostate cancer cell, an esophageal cancer cell, a head & neck cancer cell, an ovarian cancer cell, a uterine cancer cell, a testicular cancer cell, a stomach cancer cell, a colon cancer cell, a colorectal cancer cell, a skin cancer cell, a blood cancer cell, nasopharyngeal cancer cell, or a pancreatic cancer cell.

39. The method of claim 25, wherein said cancer cell is a recurrent cancer cell, a metastatic cancer cell, a non-metastatic cancer cell and/or a multi-drug resistant cancer cell.

40. The method of claim 25, wherein said cancer cell is a human cancer cell.

41. The method of claim 25, further comprising quantifying the binding of said first fusion protein, said second fusion protein and/or said antibody to determine relative amounts of said monomer, oligomer and polymer.

42. The method of claim 25, wherein said first and/or second fusion comprises at least a second ADP-ribose binding domain.

* * * * *

UNITED STATES PATENT AND TRADEMARK OFFICE
CERTIFICATE OF CORRECTION

PATENT NO.         : 9,599,606 B2
APPLICATION NO.    : 14/734780
DATED              : March 21, 2017
INVENTOR(S)        : W. Lee Kraus and Bryan A. Gibson It is certified that error appears in the above-identified patent and that said Letters Patent is hereby corrected as shown below:

In the Claims

In Claim 17, Column 65, Line 65, delete "Lad" and insert --Lacl-- therefor.

In Claim 25, Column 66, Line 43, delete "comprising comprising" and insert --comprising-- therefor.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,599,606 B2
APPLICATION NO. : 14/734780
DATED : March 21, 2017
INVENTOR(S) : W. Lee Kraus et al.

It is certified that error appears in the above-identified patent and that said Letters Patent is hereby corrected as shown below:

In the Specification

In Column 1, Lines 7-12, delete paragraph and insert:
--This invention was made with government support under grant number R01 DK058110 awarded by The National Institutes of Health. The government has certain rights in the invention.-- therefor.

Signed and Sealed this
Seventh Day of July, 2020

Andrei Iancu
*Director of the United States Patent and Trademark Office*